(12) United States Patent
Zuckerman et al.

(10) Patent No.: US 8,591,427 B2
(45) Date of Patent: Nov. 26, 2013

(54) HEART MONITORING SYSTEM OR OTHER SYSTEM FOR MEASURING MAGNETIC FIELDS

(75) Inventors: Lawrence H. Zuckerman, Livermore, CA (US); Michael X. Maida, Sunnyvale, CA (US); Dennis M. Monticelli, Fremont, CA (US); James B. Wieser, Livermore, CA (US); Jamal Ramdani, Scarborough, ME (US); Paul Mawson, Campbell, CA (US); Moulay Mohamed Ibourk, Sunnyvale, CA (US)

(73) Assignee: National Semiconductor Corporation, Santa Clara, CA (US)

( * ) Notice: Subject to any disclaimer, the term of this patent is extended or adjusted under 35 U.S.C. 154(b) by 499 days.

(21) Appl. No.: 12/927,204

(22) Filed: Nov. 9, 2010

(65) Prior Publication Data

US 2011/0152703 A1    Jun. 23, 2011

Related U.S. Application Data

(60) Provisional application No. 61/280,808, filed on Nov. 9, 2009, provisional application No. 61/332,592, filed on May 7, 2010, provisional application No. 61/356,403, filed on Jun. 18, 2010.

(51) Int. Cl.
*A61B 5/02* (2006.01)

(52) U.S. Cl.
USPC .......................................... 600/508

(58) Field of Classification Search
USPC ................................. 600/508, 518
See application file for complete search history.

(56) References Cited

U.S. PATENT DOCUMENTS 4,673,827 A   6/1987 Sommer
5,117,834 A * 6/1992 Kroll et al. .................... 600/518
5,767,668 A * 6/1998 Durand ..................... 324/117 R
2001/0028245 A1  10/2001 Li et al.
2001/0040450 A1  11/2001 Li et al.
2004/0126620 A1* 7/2004 Viehland et al. .............. 428/692
2009/0230953 A1   9/2009 Lee

FOREIGN PATENT DOCUMENTS

JP    2001028466 A    1/2001

OTHER PUBLICATIONS

Notification of Transmittal of the International Search Report and the Written Opinion of the International Searching Authority, or the Declaration dated Jun. 30, 2011 in connection with International Patent Application No. PCT/US2010/056047.
Notification of Transmittal of the International Search Report and the Written Opinion of the International Searching Authority, or the Declaration dated Jun. 30, 2011 in connection with International Patent Application No. PCT/US2010/056054.

* cited by examiner

*Primary Examiner* — Christopher D Koharski
*Assistant Examiner* — Nadia Ahmad
(74) *Attorney, Agent, or Firm* — Eugene C. Conser; Wade J. Brady, III; Frederick J. Telecky, Jr.

(57) ABSTRACT

A system includes at least one first magnetic field sensor configured to measure first and second magnetic fields. The system also includes at least one second magnetic field sensor configured to measure the second magnetic field substantially without measuring the first magnetic field. The system further includes processing circuitry configured to perform signal cancellation to generate measurements of the first magnetic field and to generate an output based on the measurements of the first magnetic field. The sensors could represent magneto-electric sensors. The magneto-electric sensors could be configured to up-convert electrical signals associated with the first and/or second magnetic fields to a higher frequency. The processing circuitry could be configured to identify one or more problems associated with a patient's heart.

16 Claims, 13 Drawing Sheets

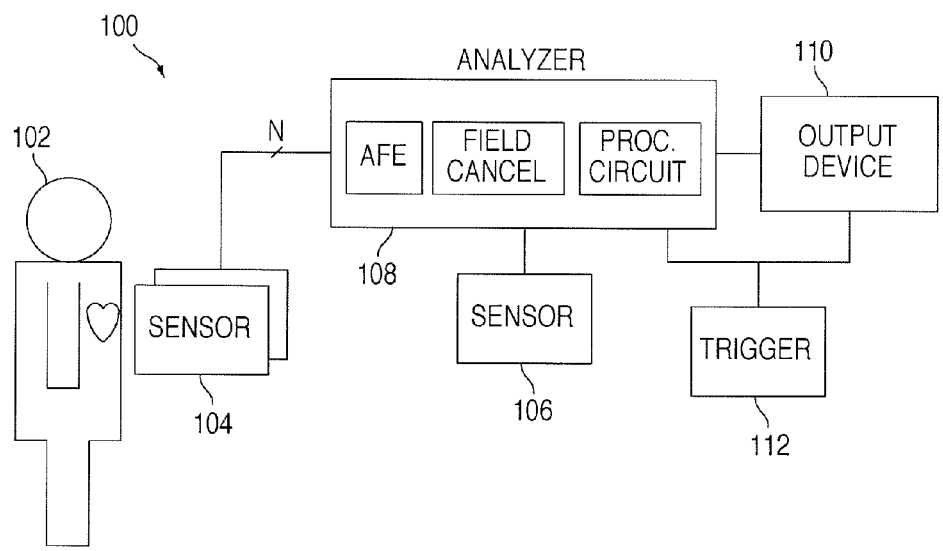
FIG. 1
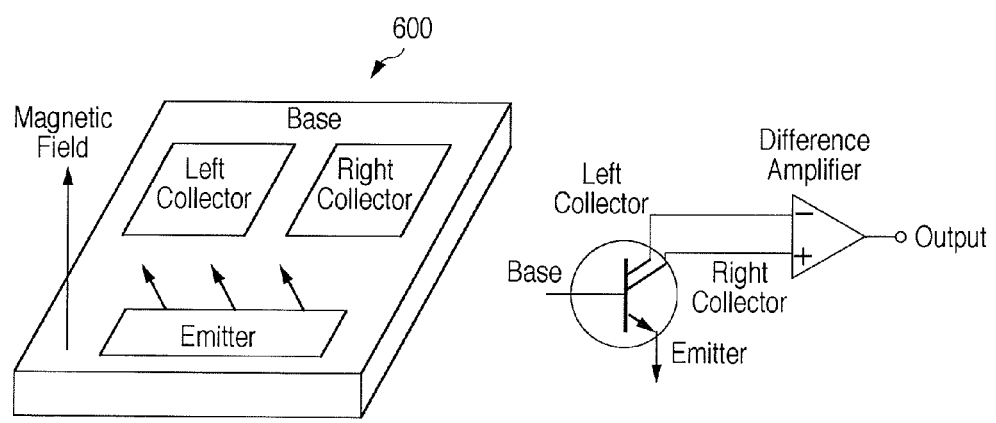
FIG. 6A   FIG. 6B ional patent applications are hereby incorporated
HEART MONITORING SYSTEM OR OTHER SYSTEM FOR MEASURING MAGNETIC FIELDS

CROSS-REFERENCE TO RELATED APPLICATIONS AND PRIORITY CLAIM

This application claims priority under 35 U.S.C. §119(e) to the following U.S. provisional patent applications:

U.S. Provisional Patent Application No. 61/280,808 filed on Nov. 9, 2009;

U.S. Provisional Patent Application No. 61/332,592 filed on May 7, 2010; and

U.S. Provisional Patent Application No. 61/356,403 filed on Jun. 18, 2010.

All three of these patent applications are hereby incorporated by reference.

TECHNICAL FIELD

This disclosure relates generally to systems that measure and analyze magnetic fields. More specifically, this disclosure relates to a heart monitoring system or other system for measuring magnetic fields.

BACKGROUND

One of the banes of modern society is that dangerous medical conditions without symptoms or risk factors go undetected, often because diagnostic tools and procedures are too expensive or time consuming for routine examinations. One prominent example is coronary disease, such as myocardial ischemia (a lack of blood flow to the heart). Instrumentation currently available in a primary care physician's office often includes electrocardiogram (ECG) equipment. ECG equipment has been used for almost a century to obtain waveforms that represent electric currents flowing within a patient's heart during its beating cycle.

The information available from ECG waveforms is limited mainly by distortions from body tissues. Numerous attempts have been made to derive definitive information from ECG data that indicates coronary disease in patients with no symptoms or risk factors. However, the expense, length of time required, and need for precise placement of probes often severely limit the use of these techniques in mass screenings. Moreover, ECG equipment often cannot detect many cases of coronary disease during a normal or routine physical examination. Owing to the high cost of more reliable tests such as stress echocardiograms and stress myocardial perfusions, patients without symptoms and/or several risk factors often do not receive such tests since they are not covered by insurance.

In contrast, magnetic fields from cardiac currents penetrate body tissues without significant or any distortion. However, these magnetic fields are extremely weak, often about 20 pico-Tesla (pT) peak-to-peak. Still, they can be measured with the aid of an extremely low-level sensor called a Superconducting Quantum Interference Device (SQUID). Various SQUID-type devices have been built, used for clinical testing, and shown to provide far more information about the condition of a patient's heart than ECG. The waveforms produced using a SQUID instrument are called magneto-cardiograms (MCGs) and resemble the waveforms of an ECG, but much more detail is available in an MCG.

Different aspects of MCG waveforms captured using a SQUID instrument have been shown to correlate reliably with various cardiac conditions. For example, T-waves can be detected clearly using a SQUID instrument, and a feature called "T-Wave Alternans" has been shown to be indicative of ischemia of the heart muscle. T-Wave Alternans refers to alternating T-waves shifting up and down in amplitude by about 20%-25%.

Although useful for reliable diagnostics, a SQUID instrument is not practical for routine clinical use. It is quite large and very expensive. It often requires a shielded room to exclude interfering magnetic fields within a spectral range from 0.1 Hz to 100 Hz. In addition, it typically has to be super-cooled so that it is not warmer than 77° K. While some SQUID-type instruments have been developed that do not required the use of a shielded room, these devices still require super-cooling, which often prevents their use in primary clinical settings.

BRIEF DESCRIPTION OF DRAWINGS

For a more complete understanding of this disclosure and its features, reference is now made to the following description, taken in conjunction with the accompanying drawings, in which:

FIG. 1 illustrates an example system for measuring magnetic fields according to this disclosure;

FIGS. 6A and 6B illustrate an example sensor in a system for measuring magnetic fields according to this disclosure;

DETAILED DESCRIPTION

Figure 2:
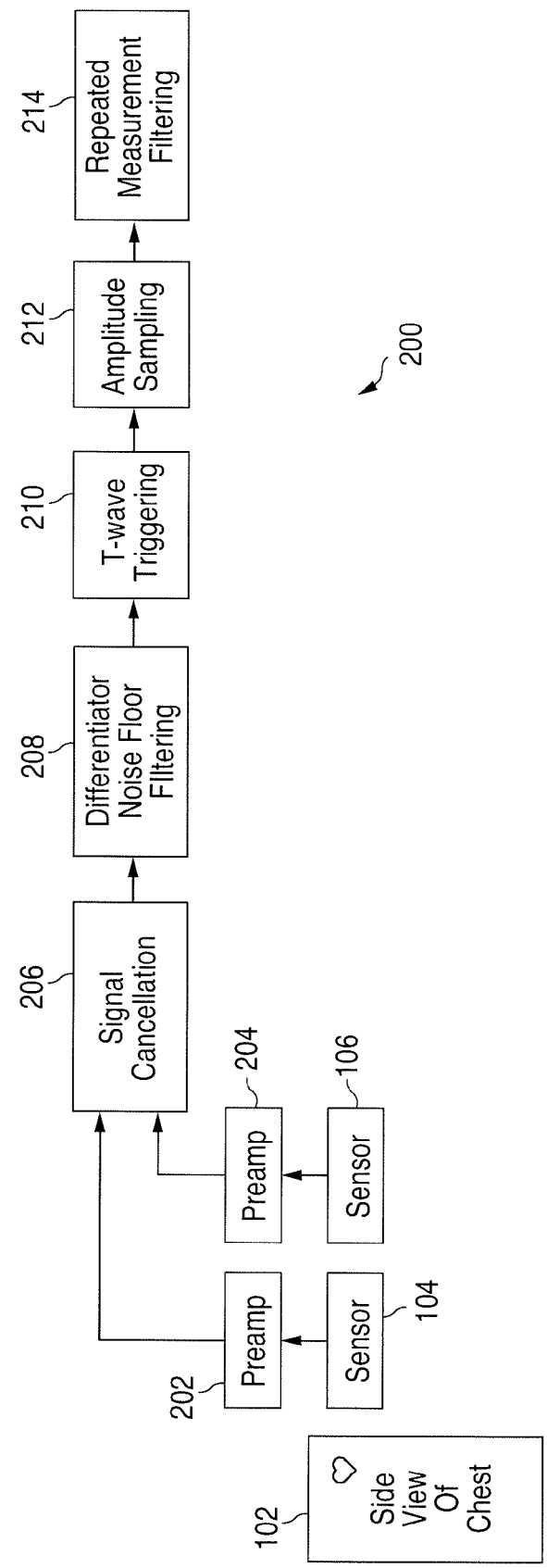
FIGS. 2 through 4 illustrate specific examples of systems for measuring magnetic fields according to this disclosure.

FIGS. 1 through 18, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Among other things, this disclosure describes various magnetic field sensors for measuring magnetic fields, such as magnetic fields from a patient's body taken during screening for heart diseases. This disclosure also describes various systems for analyzing signals from magnetic field sensors to detect specified conditions (such as myocardial ischemia or other heart diseases). These systems could perform this detection rapidly and inexpensively enough to be included as part of a routine physical examination. Since half of patients with new-onset myocardial infarctions ("heart attacks") have no symptoms before onset, these types of systems can be highly useful in detecting dangerous undiagnosed conditions in patients.

FIG. 1 illustrates an example system 100 for measuring magnetic fields according to this disclosure. In this example, the system 100 measures and analyzes magnetic fields generated by electrical currents in the heart of a patient 102. However, the system 100 could be used to measure any other magnetic fields, whether or not those magnetic fields are generated by a patient.

As shown in FIG. 1, the system 100 includes one or more magnetic field sensors 104 and one or more magnetic field sensors 106. The sensors 104 are placed near the patient 102, such as near or on the patient's chest cavity. The sensors 106 are placed away from the patient 102. The sensors 104 measure the magnetic fields around the sensors 104, which include an ambient magnetic field and a magnetic field of interest (in this case, the magnetic field generated by the patient's heart). The sensors 106 measure the magnetic fields around the sensors 106, which include the ambient magnetic field but not the magnetic field of interest. The ambient magnetic field refers to the background magnetic field in a certain area, including the Earth's magnetic field, fields generated by AC main electrical lines, electric transportation, and nearby sources of interference such as electronic equipment and magnets.

Each magnetic field sensor 104-106 includes any suitable structure for measuring a magnetic field. For example, the sensors 104-106 could represent magneto-resistive sensors, giant magneto-resistive sensors, giant magneto-tunnel junctions, magneto-electric sensors, spin-valve sensors, cesium vapor sensors, flux gate sensors, optically-pumped sensors, or micro-electro-mechanical system (MEMS) sensors. In some embodiments, the sensors 104-106 operate at room temperature or otherwise are designed so that no super-cooling is required. In general, any magnetic field sensor capable of measuring the desired magnetic fields (such as extremely weak fields like those down to 20 pT or even less) can be used. Example magnetic field sensors 104-106 are discussed below.

In particular embodiments, multiple sensors 104 and one sensor 106 could be used. For example, N sensors 104 could be placed at different positions over the patient's chest. Different sensors 104 form different "channels," and the sensor 106 can measure the ambient magnetic field for all channels. Note, however, that any other number(s) of sensor(s) 104 or 106 could be used.

The signals from the sensors 104-106 are provided to an analyzer 108, which processes the signals to perform a variety of functions depending on the implementation. For example, when used in a heart monitoring system, the analyzer 108 could identify T-waves in the patient's heart waveform and determine whether alternating T-waves differ by a threshold amount (such as between about 20% to about 40%). However, other features of the patient's heart waveform could be identified and used to identify cardiac/coronary disease or other problems.

In this example, the analyzer 108 includes analog front end (AFE) circuitry, which processes analog signals received from the sensors 104-106. The analyzer 108 also includes ambient field cancellation circuitry, which uses signals from the sensor(s) 106 to substantially reduce or cancel measurements of the ambient magnetic field in signals from the sensor(s) 104. Ideally, the output of the ambient field cancellation circuitry represents only the signals defining the magnetic field of interest, although in reality there may be noise and other distortions. In addition, the analyzer 108 includes processing circuitry that further processes and/or analyzes the signals output by the ambient field cancellation circuitry.

This represents one example of the types of components that could be used in the analyzer 108. In general, the analyzer 108 includes any suitable structure(s) for processing signals from magnetic field sensors. The analyzer 108 could be formed from hardware circuits only, or functions performed by the analyzer 108 could by implemented using software or firmware instructions. Example embodiments of the analyzer 108 are described below.

In this example, the analyzer 108 is coupled to an output device 110, which represents any suitable device through which information can be conveyed to a user like medical personnel. For example, the output device 110 could represent a display device that displays T-waves or other MCG waveforms. The display device could also present information generated by the analyzer 108, such as measurements, warnings, or other data associated with analysis of the signals from the sensors 104-106.

Optionally, the analyzer 108 and/or the output device 110 may be coupled to a triggering unit 112. The triggering unit 112 could identify various events, such as beats of the patient's heart. This information could be presented on the output device 110, used during processing or analysis of the signals in the analyzer 108, or in any other suitable manner. In particular embodiments, the triggering unit 112 could represent an ECG device. In some embodiments, an ECG device could be used simply to provide a reference signal for averaging multiple MCG heartbeat events. In other embodiments, the analyzer 108 could use the ECG signal in order to identify one or more mathematical correlations between the magnetic signal and the ECG signal. This could be done, for example, to help pull the MCG signal out of noise. Any suitable correlation could be calculated here, such as a correlation performed in the wavelet domain.

Although FIG. 1 illustrates one example of a system 100 for measuring magnetic fields, various changes may be made to FIG. 1. For example, the system 100 could be used to measure or analyze any suitable magnetic fields, including magnetic fields from another portion of a patient's body or magnetic fields not generated by a patient's body. Also, any number of magnetic field sensors, analyzers, output devices, and triggering units could be used in the system 100. In addition, the processing or analysis of the signals performed by the analyzer 108 would vary depending on, for instance, the magnetic fields being measured.

Figure 3:
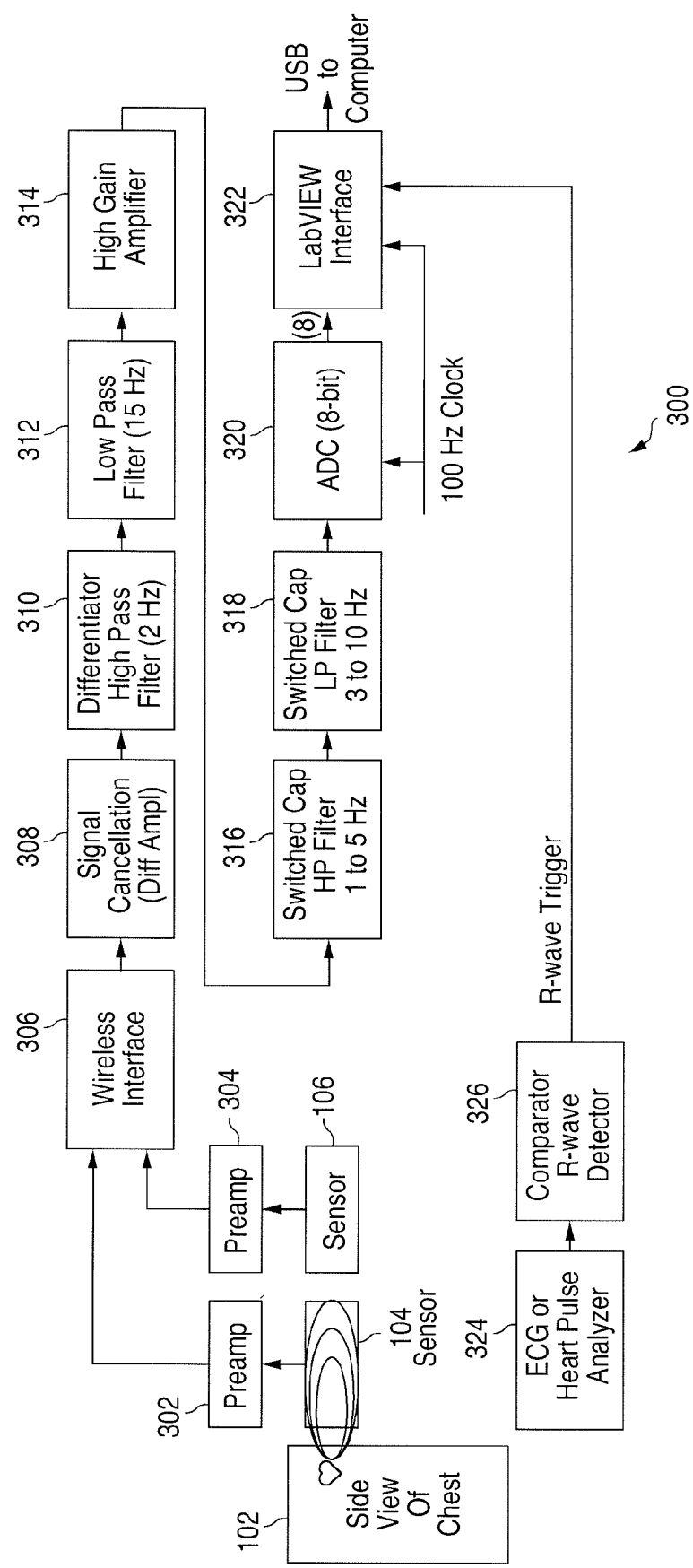
Figure 4:
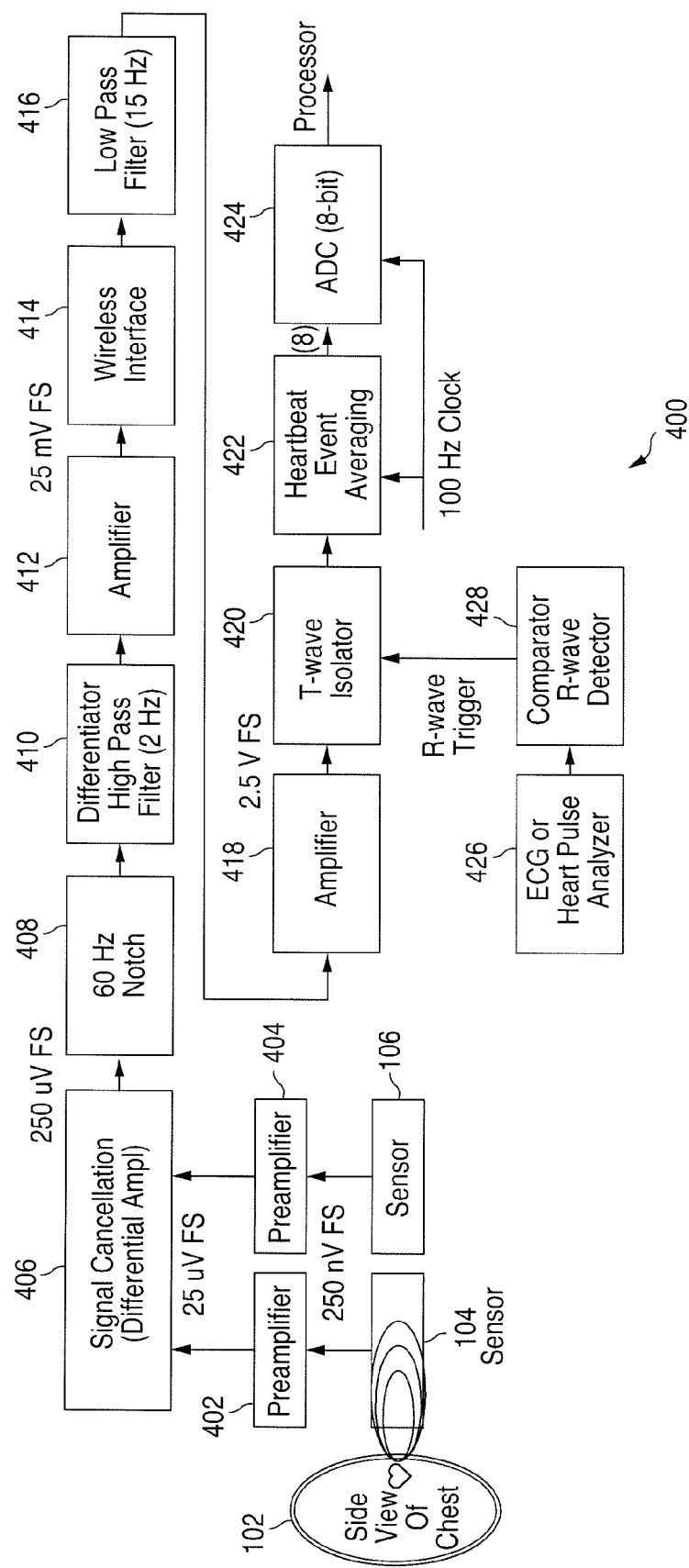

FIGS. 2 through 4 illustrate specific examples of systems for measuring magnetic fields according to this disclosure. As shown in FIG. 2, a system 200 includes the magnetic field sensors 104-106. Outputs from the sensors 104-106 are provided to and amplified by pre-amplifiers 202-204, which represent any suitable structures for performing amplification. A signal cancellation unit 206 receives the amplified outputs of the sensors 104-106. The signal cancellation unit 206 generally removes the ambient field measurements from the heart plus ambient field measurements, thereby substantially isolating the measurements of the heart's magnetic field. The signal cancellation unit 206 includes any suitable structure for performing signal cancellation using two or more signals, such as a difference amplifier. The signal cancellation unit 206 may include appropriate adjustments for gain, phase, and directional response matching of the sensor(s) 106 relative to the sensor(s) 104.

In this example, the output of the signal cancellation unit 206 is processed to identify amplitudes of the patient's T-waves, which can be done to support the T-wave Alternans test. Considering each T-wave as a pulse, its Fourier Trans-form places its spectrum mainly at DC. With advantageous signal processing, the spectrum containing sufficient information can exist at around 4 Hz to 5 Hz, thus avoiding the very highest noise level in the lower portion of the heart wave spectrum between 0.1 Hz and 1 Hz. With virtually no signal processing following the signal cancellation unit 206, the noise spectrum could extend down to 0.1 Hz, and the waveform of the patient's heart output by the signal cancellation unit 206 would be riding on a large noise floor. Almost all of the noise could have a low frequency, meaning its time slope would be very small. Thus, the original overall DC level of the desired waveform can be obliterated. However, higher frequency components, including larger-value time slopes (both positive and negative), of most features can be minimally affected.

To process the signal output by the signal cancellation unit 206, the system 200 includes a differentiator noise floor filter 208, a T-wave triggering unit 210, an amplitude sampling unit 212, and a repeated measurement filter 214. Using the differentiator noise floor filter 208, the waveform from the signal cancellation unit 206 can be differentiated, thus removing most or all of the original amplitude information (including low frequency noise) but containing the slope values (including those of the rising and falling components of the peak-to-peak T-wave). This could effectively translate the T-wave signal up to 4 Hz or so, away from the higher, DC noise floor. The T-wave triggering unit 210 identifies the locations of T-waves in the differentiated waveform, such as by using the locations of preceding QRS complexes (sets of deflections also contained in the waveform). The amplitude sampling unit 212 measures the amplitudes of the identified T-waves in the differentiated waveform, such as at their positive and negative peaks. The repeated measurement filter 214 averages the measured amplitudes of the identified T-waves.

The differentiator noise floor filter 208 includes any suitable structure for differentiating a waveform. The T-wave triggering unit 210 includes any suitable structure for identifying locations of T-waves. The amplitude sampling unit 212 includes any suitable structure for determining the amplitude of a signal. The repeated measurement filter 214 includes any suitable structure for filtering or averaging amplitude measurements.

As noted above, if an ischemic heart muscle condition exists, alternating beat T-waves can have the same period but differing amplitudes, so the T-waves would have differing slope values. For a heart rate of 80 beats per minute, the differentiated T-wave power may exist in a narrow band around 4 Hz with about the same amplitude as the original, undifferentiated T-wave. Higher heart rates with the same amplitude T-waves would produce higher amplitude differentiated T-waves. One objective of the signal analysis performed in FIG. 2 may be to take advantage of known pulse positions and restrict the spectrum as much as possible without impairing the ability to measure pulse height. That is, one goal can be to clearly distinguish, over a three-minute or other screening period, between (i) a uniform amplitude (beat-to-beat) and (ii) a 20%-25% (or other) amplitude shift above and below the mean with alternating beats. The differentiated T-waves for alternating sets of beats may therefore yield higher and lower amplitudes on average. The repeated measurement filter 214 can average the measured amplitudes of alternating T-waves, and outputs of the filter 214 can be used to determine whether the average amplitudes of alternating T-waves indicate ischemia of the heart muscle. For a three-minute test, there could be a total of 240 heartbeats, and alternate beat T-waves can be averaged separately. Averaging by multiple readings could reduce the effective noise floor further, such as by an additional 21 dB from approximately 10 pT to 1 pT.

The system 200 can therefore be used to perform a three-minute (or other length) T-wave Alternans test as a primary clinical mass screening tool. However, the system 200 need not be restricted to analyzing T-wave pulse heights to check for myocardial ischemia. Any other or additional conditions can be tested for using the system 200. For example, clinical studies using MCG devices have linked various features of MCG waveforms to various other dangerous conditions. Any condition indicated by waveform features having sufficiently high-amplitude spectral components, such as those above 10 Hz, could be detected by the system 200. As particular examples, the system 200 could be used to detect the onset of arrhythmic and ischemic diseases in a very early stage with high accuracy for both acute and asymptomatic patients, including arrhythmia, ischemia, angina pectoris, and cardiac micro-vascular diseases.

As shown in FIG. 3, a system 300 includes the magnetic field sensors 104-106, and outputs of the sensors 104-106 are provided to pre-amplifiers 302-304. The pre-amplifiers 302-304 are coupled to a wireless interface 306, which reduces or eliminates asymmetric wiring and field disturbances. Any suitable wireless scheme could be used, such as infrared, radio frequency (RF), or other technology. A signal cancellation unit 308, such as a difference amplifier, receives input from the wireless interface.

A high-pass (HP) filter 310 and a low-pass (LP) filter 312 process an output of the signal cancellation unit 308. The filters 310-312 represent any suitable filters, such as a 2 Hz differentiator high-pass filter and a 15 Hz low-pass filter. A high-gain amplifier 314 amplifies an output of the filter 312, and additional filters 316-318 filter an output of the amplifier 314. The amplifier 314 includes any suitable structure for providing amplification. The filters 316-318 represent any suitable filters, such as a 1-5 Hz switched capacitor high-pass filter and a 3-10 Hz switched capacitor low-pass filter.

An analog-to-digital converter (ADC) 320 converts an analog output of the filter 318 into digital values. The digital values are provided to an interface 322, which provides the digital values to other components for analysis. The ADC 320 includes any suitable structure for converting analog values into digital values. The interface 322 includes any suitable structure for outputting data. In this example, the ADC 320 is an eight-bit converter, and the interface 322 is a LABVIEW interface that communicates over a USB connection with a host device.

An ECG or heart pulse analyzer 324 and an R-wave detector 326 are used to trigger on T-waves in the patient's heart signal. An R-wave is a type of deflection in the waveform of the patient's heart signal. This can be done to separately synchronize pertinent data from multiple heartbeats, even though the patient's heart rate may vary from one beat to the next.

As shown in FIG. 4, a system 400 includes the magnetic field sensors 104-106 coupled to pre-amplifiers 402-404, which are coupled to a signal cancellation unit 406. A notch filter 408 filters an output of the signal cancellation unit 406. The notch filter 408 represents any suitable filter, such as a 60 Hz and harmonics notch filter. A high-pass filter 410 and an amplifier 412 process an output of the filter 408, and a wireless interface 414 is coupled to the amplifier 412. The wireless interface 414 provides an input to a low-pass filter 416, which is coupled to an amplifier 418.

A T-wave isolator 420 isolates T-waves in an input signal using input from an ECG or heart pulse analyzer 426 and an R-wave detector 428. A heartbeat event averaging unit 422 averages signals from the T-wave isolator 420, such as by isolating and measuring alternating beat T-waves using peak detection and sample and hold circuits. An ADC 424 converts an analog output of the T-wave isolator 420 into digital values, which can be further processed.

Although FIGS. 2 through 4 illustrate specific examples of systems for measuring magnetic fields, various changes may be made to FIGS. 2 through 4. For example, multiple channels can be used in each system 200-400. Each channel could include at least one magnetic field sensor 104 (for measuring the heart magnetic field at one location plus the ambient magnetic field), along with a pre-amplifier, signal cancellation unit, and other circuitry shown in the signal path of FIGS. 2 through 4. Multiple magnetic field sensors 104 could be arranged in a grid to measure multiple positions over the patient's chest, which may help to ensure that at least one of the magnetic field sensors 104 measures the largest T-wave signal. Also, multiple sensors at each location can be used to add correlated signal voltage but uncorrelated sensor noise power values, which can help to further increase the signal-to-noise ratio (SNR). In addition, a single ambient field sensor 106 can be used to measure the ambient field, regardless of the number of channels used.

Also note that the functional divisions shown in FIGS. 2 through 4 are for illustration only. Various components in each figure could be combined, omitted, or further subdivided and additional components could be added according to particular needs. As one example, various components in each figure could be combined into a single functional unit, such as when certain functions are implemented using a digital signal processor. As another example, the differentiator noise floor filter 208 could be implemented as an analog differentiating circuit, or the time derivative could be calculated after an analog-to-digital converter captures the output of the signal cancellation unit 206. As yet another example, the differentiator noise floor filter 208 could be omitted, which may increase the amount of processing time or processing power needed to analyze the captured data. Moreover, the averaging may be moved after the ADC into the digital domain. As still other examples, a frequency up-converter (such as a chopper) could be used as the front end device, and a tracking filter or lock-in amplifier could be used to support signal band filtering. In particular embodiments, each of the systems 200-400 could be implemented as a handheld MCG device that includes sensor elements along with instrumentation amplifiers, Sigma-Delta analog-to-digital converters, filters, and a DSP.

Figure 5:
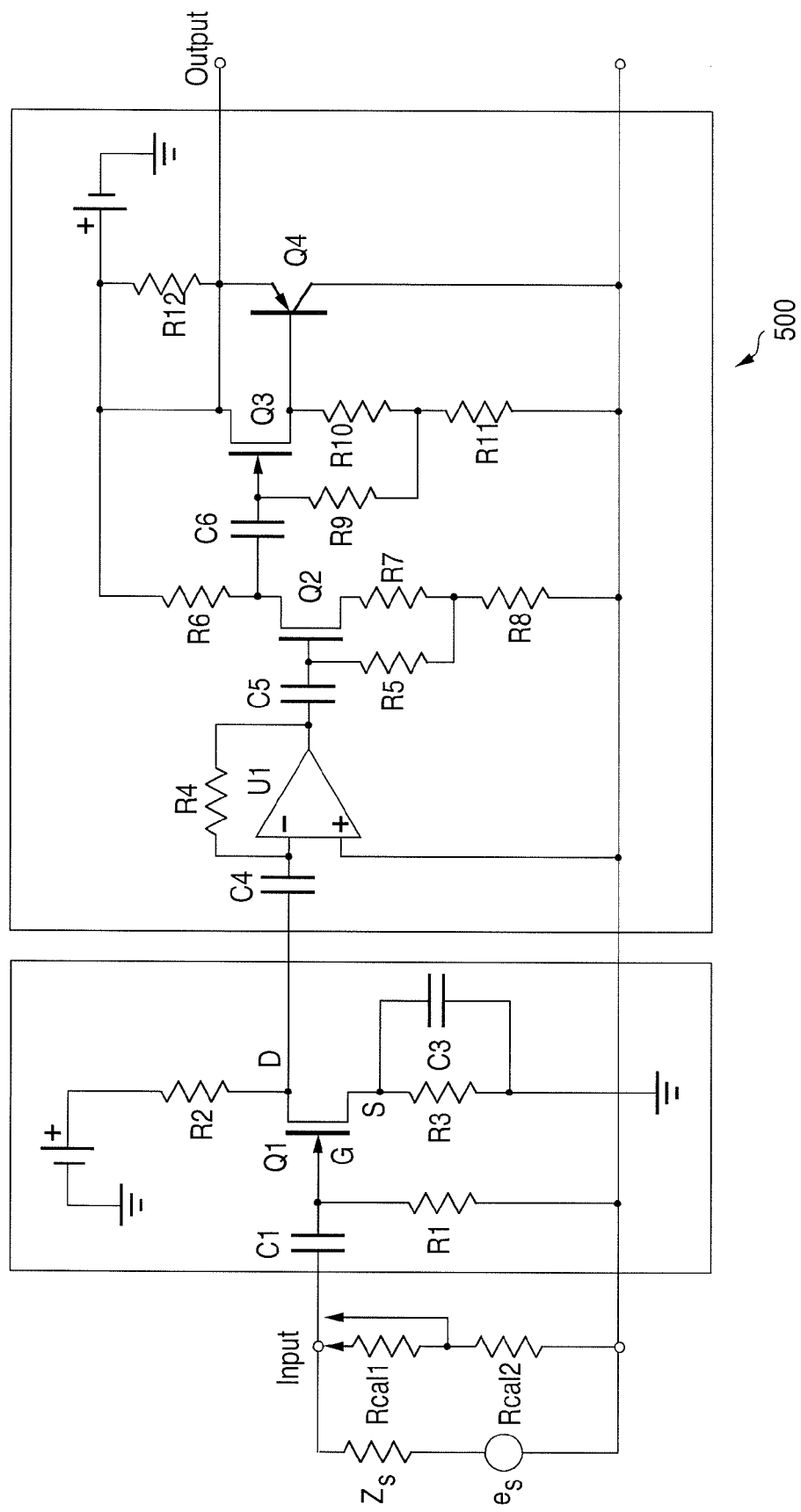
FIG. 5 illustrates an example pre-amplifier in a system for measuring magnetic fields according to this disclosure.

In FIGS. 2-4, the pre-amplifiers may need an extremely low noise and an extremely high impedance input. FIG. 5 illustrates an example pre-amplifier 500 in a system for measuring magnetic fields according to this disclosure. This pre-amplifier 500 represents a high-impedance JFET amplifier. In particular implementations, this pre-amplifier 500 could have an equivalent input noise spectral density of about 1 nV/Hz$^{0.5}$ at 3 Hz. More information about this type of device can be found in Levinzon, "Ultra Low Noise High-Input Impedance Amplifier for Low Frequency Measurement Applications," IEEE Trans. Circuits & Systems, V55 No. 7, 2008 (which is hereby incorporated by reference). Note, however, that any other suitable pre-amplifier could be used.

In any of the systems shown above, any suitable type of magnetic field sensor could be used as the sensor(s) 104 and/or the sensor(s) 106. The following describes various types of sensors that could be used. These types of sensors are provided as examples only. The systems described above (and similar systems) could use any suitable sensors capable of measuring the desired magnetic fields. For example, the systems could use magneto-resistive sensors, such as magneto-resistive elements manufactured by NVE or MICROMAGNETICS.

Another example sensor can be formed from giant magneto-resistive devices, such as those that use magneto-tunnel junctions (MTJs). Example magneto-tunnel junctions can be formed from CoFeB/MgO/CoFeB [$(Co_{70}Fe_{30})_{20}B_{80}$], which can have high magneto-resistive ratios at room temperature and sensitivities in the hundreds of pT/Hz$^{0.5}$. Introduction flux guides can improve sensitivities down to 90 pT/Hz$^{0.5}$, for example. Further improvements in noise suppression (1/f, shot and thermal) can lead to sub-pT/Hz$^{0.5}$ values. To form this type of structure, material can be sputtered at room temperature (magnetron) and can be annealed at 360° C. for 30 to 60 minutes under a high magnetic field. Ten to twelve layers can be formed depending on the design, including contact layers based on Ta, CuN, PtMn, CoFe, or Ru MTJ/Ta on SiO$_2$ on Si substrates. The annealing can be compatible with BEOL (360° C. or less than 400° C.) under an intense magnetic field (such as 8 KOe). The sensor size could be from 1 um×1 um up to 3 um×8 um, and it could support BEOL integration with BiCMOS-based low noise amplifiers (LNAs). Additional details regarding this type of sensor can be found, for example, in "Low frequency picotesla field detection using hybrid MgO based tunnel sensors," Appl. Phys. Lett. 91, 102504 (2007) (which is hereby incorporated by reference).

FIGS. 6A and 6B illustrate another example sensor 600 in a system for measuring magnetic fields according to this disclosure. In this example, a highly-sensitive magnetometer can be implemented using a dual collector NPN transistor on a low-noise process (such as a BiCMOS process). The NPN transistor could be formed on a semiconductor-on-insulator (SOI) substrate, such as a silicon substrate with a buried oxide layer.

Figure 7:
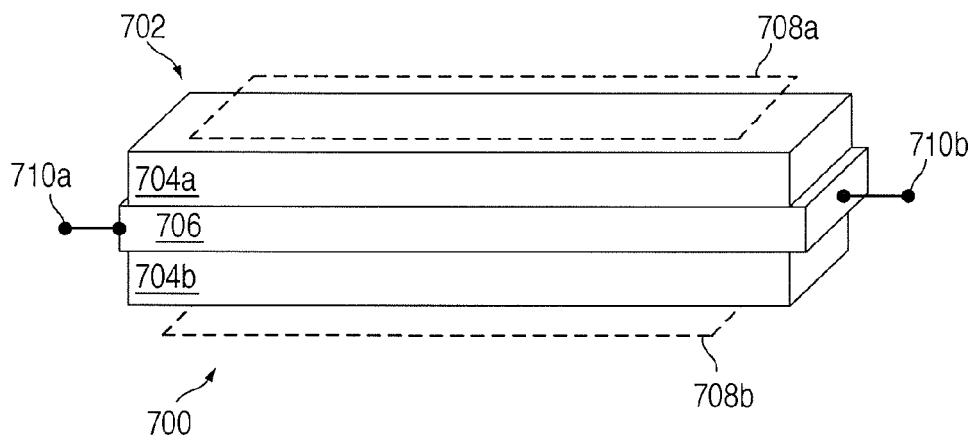
FIGS. 7 and 8 illustrate example magneto-electric sensors in a system for measuring magnetic fields according to this disclosure.
Figure 8:
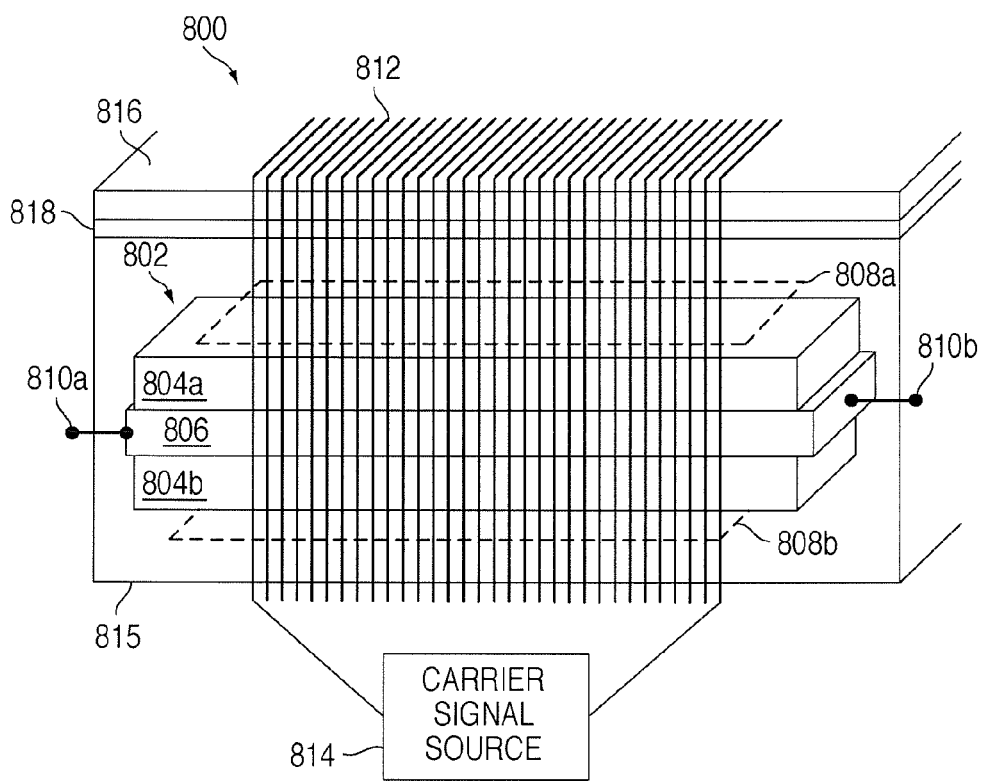

Yet another example sensor is a magneto-electric sensor. FIGS. 7 and 8 illustrate example magneto-electric sensors in a system for measuring magnetic fields according to this disclosure. In FIG. 7, a sensor 700 includes a sensor stack 702 having alternating magneto-strictive and piezo-electric layers. In this example, layers 704a-704b are magneto-strictive, and layer 706 is piezo-electric. The magneto-strictive layers 704a-704b lengthen and shorten depending on an ambient magnetic flux density value. As the magneto-strictive layers 704a-704b are physically attached (such as laminated) to the piezo-electric layer 706, the piezo-electric layer 706 also lengthens and shortens. The piezo-electric effect results in a charged capacitance whose voltage is an analog version of surrounding magnetic field measurements.

While two magneto-strictive layers 704a-704b and one piezo-electric layer 706 are shown in FIG. 7, the sensor 700 could include any number of magneto-strictive and piezo-electric layers. The sensor 700 could, for example, include tens or hundreds of magneto-strictive and piezo-electric layers. Additional details regarding this type of sensor can be found, for example, in "Detection of pico-Tesla magnetic fields using magneto-electric sensors at room temperature," Appl. Phys. Lett. 88, 062510 and U.S. Pat. No. 7,023,206 (both of which are hereby incorporated by reference).

Each magneto-strictive layer 704a-704b could be formed from any suitable magneto-strictive material(s), such as TERFENOL D or METGLAS. Each piezo-electric layer 706 could be formed from any suitable piezo-electric material(s), such as quartz or PZT (lead zirconate titanate). Each of these layers could also be formed in any suitable manner. For instance, one or more magneto-strictive layers could be formed by sputtering the magneto-strictive material(s) onto a piece of piezo-electric material.

One or more permanent magnets 708a-708b are used in the sensor 700 to immerse the magneto-strictive layers in a biasing magnetic field, such as a substantially constant time-invariant direct current (DC) magnetic field of considerable amplitude. When the biasing magnetic field of a correct value has field lines parallel to the longitudinal direction of the layers 704a-704b, the layers 704a-704b lengthen and shorten in proportion with the instantaneous value of the component of the magnetic field parallel to the longitudinal direction of the layers 704a-704b. As a result, the lengthening and shortening of the magneto-strictive layers 704a-704b (and thus the piezo-electric layer 706) is proportional to the surrounding magnetic field. Each permanent magnet 708a-708b could include any suitable magnetic structure. Note that while two permanent magnets 708a-708b are shown in specific positions in FIG. 7, the sensor 700 could include one or more than two permanent magnets in any suitable location(s).

Electrical connections 710a-710b provide electrical signals from the sensor 700 to external components. For example, the connections 710a-710b could be coupled to external signal processing circuitry. The connections 710a-710b include any suitable structures providing electrical connectivity to the sensor 700.

The magneto-electric sensor 700 is a passive device that converts a magnetic field B into an electric signal (voltage). The pT sensitivity of the sensor 700 could be around 10 Hz, and the sensor size could be 16 mm×16 mm×2 mm. Stand-alone sensor designs are possible, and MEMS technology can be used. As a particular example, a sensor could be formed by sputtering TERFENOL-D (Tb0.3Dy0.7Fe1.92) and PZT for BEL integration.

Another example magneto-electric sensor that could be used is shown in FIG. 8. In particular, FIG. 8 illustrates an example magneto-electric sensor 800 with injected up-conversion or down-conversion. The sensor 800 can be used in an AFE architecture to deliver a signal having an improved SNR compared to conventional magneto-electric sensors. The sensor shown in FIG. 7 and its associated conditioning electronics often have a relatively high noise floor. This noise floor makes it more difficult to identify a weak signal of interest (such as the weak magnetic field from a patient's heart).

As shown in FIG. 8, the sensor 800 includes a sensor stack 802 having alternating magneto-strictive and piezo-electric layers. While two magneto-strictive layers 804a-804b and one piezo-electric layer 806 are shown in FIG. 8, the sensor 800 could include any number of magneto-strictive and piezo-electric layers. One or more permanent magnets 808a-808b are used in the sensor 800, and electrical connections 810a-810b provide electrical signals from the sensor 800 to external components.

The sensor 700 would act essentially as an AC generator in series with a small value capacitor. The effective capacitance of the sensor 700 varies relatively little, such as from about 700 pF at 3 Hz to about 300 pF at 50 kHz. However, the reactance of the sensor 700 varies widely, and the reactance of this sensor 700 becomes very large at low frequencies. This makes it difficult to transfer an extremely weak signal's power to the signal processing circuitry, which itself often needs an extremely high input impedance. Unlike piezo-electric elements used in electronic circuitry for frequency control and filters, the sensor 700 can display a large change of resistance. For instance, the sensor 700 could have a resistance of several mega-Ohms at a few Hertz, a resistance of about 300 kΩ at 100 Hz, and a resistance of about 1 kΩ at 40 kHz. Such large resistance variation implies a large variation of how signal power can be extracted from the sensor 700.

In contrast, the sensor 800 can implement up-conversion to obtain a stronger signal from the sensor 800. As noted above, the permanent magnet(s) 808a-808b can generate a biasing magnetic field, which sensitizes the sensor 800 so that the sensor 800 can accurately measure the surrounding magnetic field. The sensor 800 also uses an additional magnetic field to substantially reduce or cancel the biasing magnetic field generated by the permanent magnet(s) 808a-808b at certain times, effectively desensitizing the sensor 800 during those times. This additional magnetic field can be generated using an electromagnet, which in this example is formed using a solenoid 812 coupled to a carrier signal source 814. The carrier signal source 814 generates a drive signal that drives the electromagnet, such as a current that flows through the solenoid 812, to create the additional magnetic field. The drive signal has a frequency that causes the electromagnet to repeatedly turn on and off, which repeatedly sensitizes and desensitizes the sensor 800. The solenoid 812 includes any suitable structure having a suitable number of windings, and the solenoid 812 could be formed from any suitable conductive material(s). The carrier signal source 814 includes any suitable structure for generating a drive signal at a specified frequency.

The drive signal through the solenoid 812 turns the electromagnet on and off at a specified carrier frequency rate. The carrier frequency can be much higher in frequency than the sensed magnetic field's highest frequency of interest, such as approximately 10 kHz to approximately 50 kHz for a 3 Hz signal of interest. This causes the electromagnet to cyclically turn on to cancel the biasing magnetic field and turn off to restore the biasing magnetic field, which repeatedly desensitizes and sensitizes the sensor 800. For instance, a carrier signal could supply adequate current to cancel the biasing magnetic field of the permanent magnets 808a-808b during half of a carrier cycle and no current (restoring the biasing magnetic field) during the other half of the carrier cycle.

Effectively, this modulates the biasing magnetic field with the carrier signal. The sensor 800 becomes an up-converting heterodyne mixer, and a targeted low frequency signal (such as 3 Hz) leaves the sensor 800 as coherent sidebands near the higher carrier frequency. At these higher sideband frequencies, the reactance of the piezo-capacitance of the sensor 800 is much smaller compared to the piezo-capacitance of the sensor 800 at the lower frequency (such as 12 kΩ versus 100 MΩ), and the series resistance is much smaller. The series reactance of the sensor 800 is low enough that it could be cancelled with a series-resonating inductor, thus leaving only the series resistance of the sensor 800. This permits the sensor 800 to deliver a signal with orders of magnitude more signal power.

In this example, a sensor enclosure 815 encasing other components of the sensor 800 can be split or divided so that its lid 816 or other portion is electrically separated from the remainder of the enclosure 815. This could be done using a dielectric material 818, such as KAPTON polyimide tape. This can help to prevent an unwanted short-circuited secondary turn. The enclosure 815 could be formed from any suitable material(s), such as aluminum. Note that the placement of two permanent magnets 808a-808b inside the enclosure 815 is for illustration only. Any number of permanent magnets could be used within or outside of the enclosure 815, and the magnet(s) could be placed in any suitable position(s). Also note that the windings of the solenoid 812 are placed outside the enclosure 815 in FIG. 8. Again, this is for illustration only. The solenoid's winding could be placed in any other suitable location, such as inside the enclosure 815. In addition, the use of a solenoid winding is for illustration only. Any other structure(s) forming an electromagnet could be used to substantially or completely cancel the biasing magnetic field, such as Helmholz coils.

The sensor 800 can be used in an AFE or other architecture to deliver a signal having an improved SNR compared to conventional magneto-electric sensors. The sensor 800 can make more output power available to AFE or other circuitry, reduce or avoid the need for extremely high input resistances, and/or reduce or avoid 1/f noise present at lower frequency bands of interest (such as around 3 Hz). This is accomplished by converting the lower-frequency signal of interest to a higher-frequency signal within the sensor 800 itself, as opposed to chopping the lower-frequency signal to heterodyne it to a higher frequency outside the sensor 800 after the lower-frequency signal has passed out of the sensor 800 through a very high impedance and through (what is for low frequencies) the noisiest region of the sensor.

The up-conversion functionality is useful since, with a much higher front-end frequency, the reactance from the sensor's series capacitance drops by several orders of magnitude, providing a much higher-powered signal to a pre-amplifier or other signal processing circuitry. Also, the signal processing circuitry can have much less noise at higher frequencies than at low frequencies like 3 Hz. In particular embodiments, when used in a heart monitoring application, the signal strength from the sensor 800 may be so high and the noise is so low that all or a substantial portion of a patient's heart signal can be measured, eliminating the need to perform significant amounts of signal processing to identify the patient's T-waves. This may also help to reduce the time needed to test a patient, such as from three minutes to thirty seconds.

In some embodiments, using a combination of one or more permanent magnets 808a-808b to create the biasing field that sensitizes the sensor 800 and an electromagnet to cancel this field to desensitize the sensor 800 may be superior to using just an electromagnet by itself. This is because the electromagnet with its carrier noise is turned off during the half-cycles when the sensor 100 is active, leaving only the inherently quiet permanent magnet(s). When the electromagnet is (fully) energized, the sensor is inactive, so the electromagnet noise is of no consequence.

Figure 9:
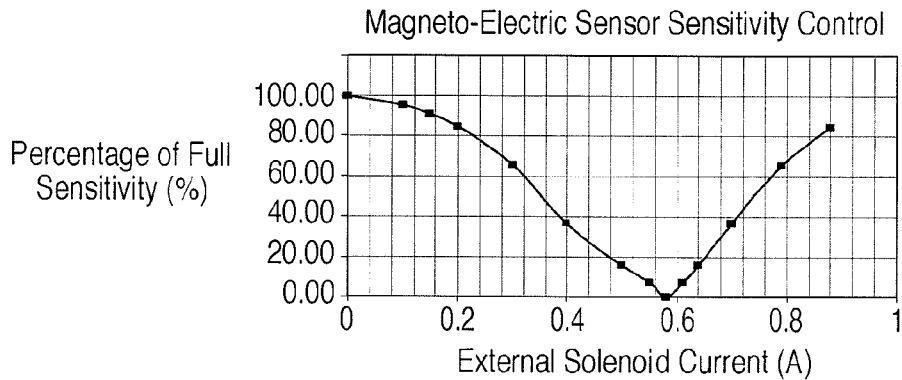
FIG. 9 illustrates an example relationship between sensor sensitivity and electromagnet coil current in a magneto-electric sensor according to this disclosure.

As noted above, the biasing magnetic field from the magnets 808a-808b can be reduced or cancelled using the electromagnet. FIG. 9 illustrates an example relationship between sensor sensitivity and electromagnet coil current in a magneto-electric sensor according to this disclosure. As shown in FIG. 9, the sensor's sensitivity versus electromagnet coil current can be a generally well-behaved function. In this example, as the current through the solenoid 812 increases from 0 A to 0.58 A, the field from the electromagnet gradually cancels out the field from the permanent magnets 808a-808b, reducing the sensor's sensitivity to zero. Then, as the current continues to increase, the net magnetic field restores the sensor's sensitivity.

Note that the sensor's sensitivity versus current and net magnetic field is substantially linear over a wide range. Gain variation being linear with current implies that the transfer characteristic is square law. This indicates that, for example, an approximately 10 kHz to approximately 50 kHz carrier signal operating within this range can make an excellent square law mixer. Also note that the behavior shown in FIG. 9 holds for a specific implementation of the sensor 800. Other implementations of the sensor 800 could have other behaviors. For instance, the behavior of the sensor 800 could vary based on the turn density of the solenoid 812.

FIGS. 10 through 14 illustrate details of an example up-conversion in a magneto-electric sensor according to this disclosure. In particular, FIGS. 10 through 14 illustrate up-conversion details for a specific implementation of the sensor 800. In the specific implementation, the solenoid 812 has an inductance of about 300 μH, and the carrier signal source 814 provides a carrier signal ranging from 0 A to about 0.6 A at a frequency of 20 kHz. Also, the sensor 800 generates a 3.5 mV peak-to-peak signal based on a magnetic field from nearby 60 Hz electrical lines.

Figure 10:
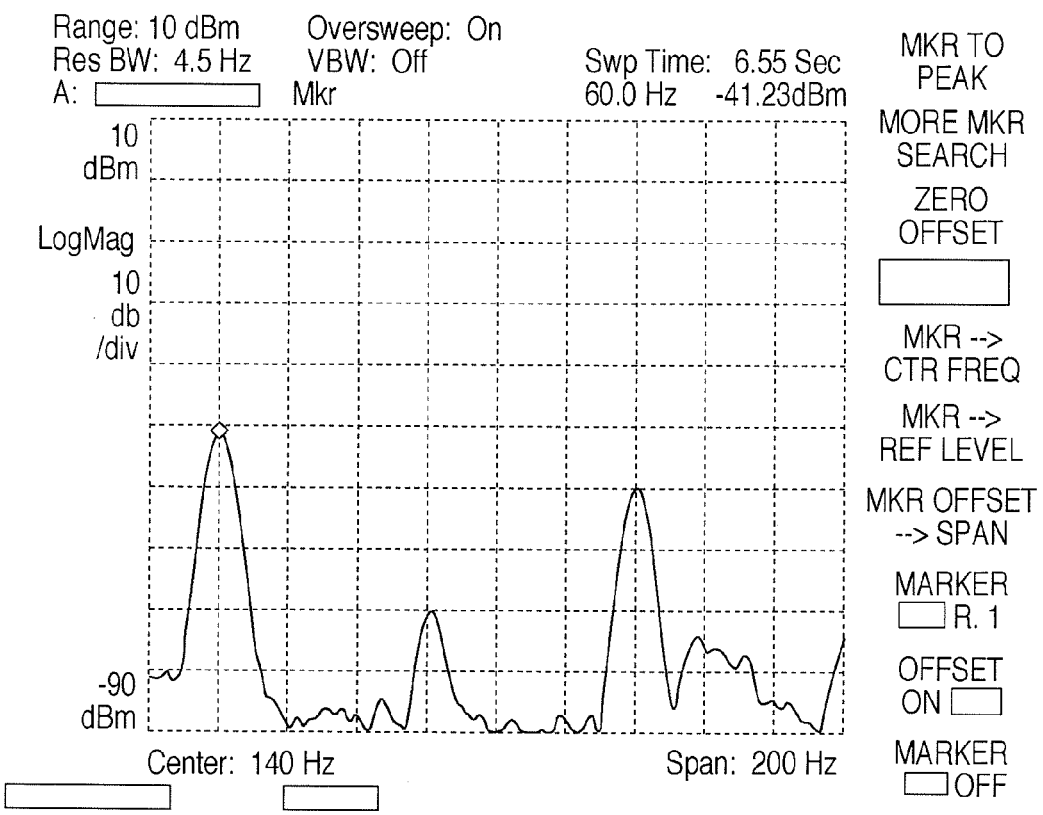
FIGS. 10 through 14 illustrate details of an example up-conversion in a magneto-electric sensor according to this disclosure.

FIG. 10 shows the sensor output when the sensor 800 is connected to a spectrum analyzer with a 1MΩ input resistance. The analyzer is set to examine the baseband signal, and the carrier signal source 814 is turned off. FIG. 10 therefore shows the output of the sensor 800 without up-conversion. As can be seen here, a 60 Hz component (the left peak) shows at −41 dBm on the scale. Also shown are second, third, and fourth harmonics.

Figure 11:
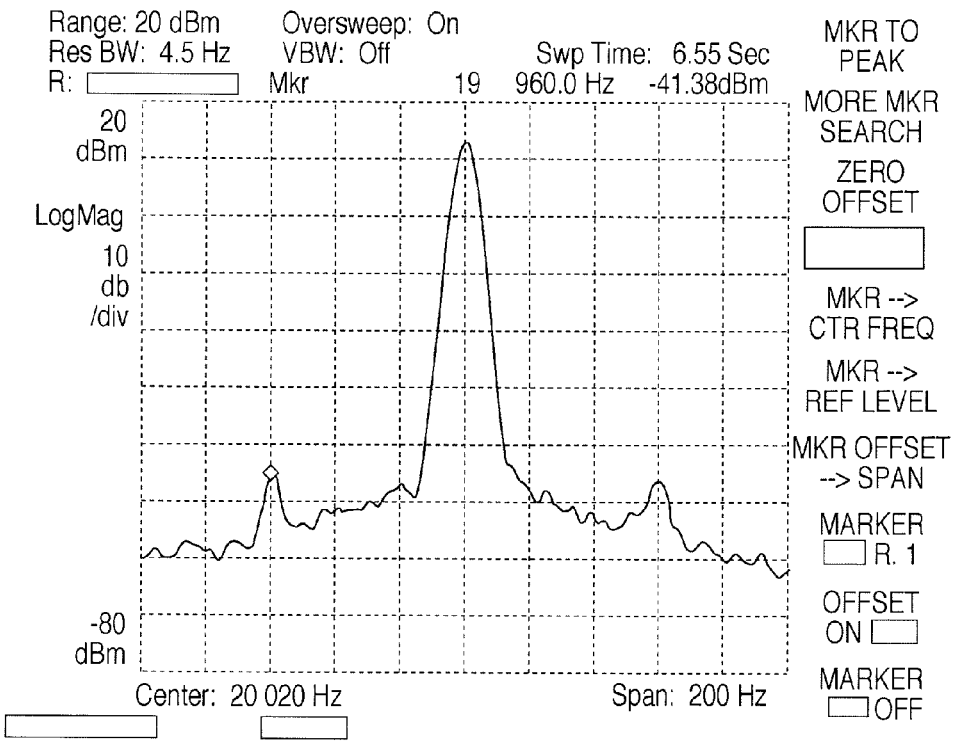

In FIG. 11, a 20 kHz carrier signal has been applied to the solenoid 812 by the carrier signal source 814, and the spectrum analyzer is adjusted to view the power spectrum centered on the carrier frequency. The sensor output has been connected to the spectrum analyzer through an inductor whose reactance cancels the capacitive reactance of the sensor (forming a series tuned circuit). Between the series inductor and the spectrum analyzer input, a shunt resistor to ground of the same value as the sensor resistance reduces the signal voltage by a factor of two. The carrier signal is seen as the large central peak, where the carrier level is shown at +13 dBm. This corresponds to an RMS voltage at 50Ω of about 1V or about 2.83V peak-to-peak relative to a sine wave. Also shown in FIG. 11 are two sidebands at +60 Hz and −60 Hz (the left and right peaks), which represent the up-converted signal of interest from baseband. The level of each sideband is about 3 dB to 4 dB lower than the 60 Hz baseband signal shown in FIG. 10. However, these two sidebands are coherent, and they can be synchronously demodulated (following a suitable amount of amplification), and their sum can be 6 dB stronger than each separate component. Thus, there is an effective conversion gain of 2 dB to 3 dB in this example. Not shown are the results of numerous tests for which sensors were inside a calibrated solenoid fed by a signal generator, in order to make absolute measurements of sensor output voltage versus magnetic flux density.

Another advantage with the sensor 800 is the reduction of sensor series capacitive reactance from about 100MΩ and reduction of series resistance from several mega-Ohms relative to a 3 Hz baseband signal to about 25 kΩ reactance and about 2 kΩ resistance relative to a 20 kHz carrier and sidebands. The advantage is far greater considering that as shown above it is practical from about 20 kHz to at least about 40 kHz to apply a series inductance to cancel the reactance, leaving only the transducer resistance of about 2 kΩ. Table 1 shows possible impedance, reactance, and other values for a particular implementation of this sensor 100.

TABLE 1

| Freq | Z Mag | Z Phase | Resistive | Reactive | Resonant L (Henries) |
| --- | --- | --- | --- | --- | --- |
| 100 | 2.891M | −84.05 | 299686 | −2875425 | 4576.516 |
| 1000 | 338.6K | −82.17 | 46129 | −335443 | 53.389 |
| 2000 | 180.9K | −82.36 | 24051 | −179294 | 14.268 |
| 3000 | 125.12K | −82.49 | 16353 | −124047 | 6.581 |

TABLE 1-continued

| Freq | Z Mag | Z Phase | Resistive | Reactive | Resonant L (Henries) |
|---|---|---|---|---|---|
| 4000 | 96.9K | −82.59 | 12497 | −96091 | 3.823 |
| 5000 | 79.24K | −82.67 | 10110 | −78592 | 2.502 |
| 6000 | 67.23K | −82.76 | 8473 | −66694 | 1.769 |
| 7000 | 58.44K | −82.83 | 7294 | −57983 | 1.318 |
| 8000 | 51.72K | −82.91 | 6384 | −51325 | 1.021 |
| 9000 | 46.52K | −83 | 5669 | −46173 | 0.817 |
| 10000 | 42.28K | −83.09 | 5087 | −41973 | 0.668 |
| 10000 | 42.86K | −83.34 | 4971 | −42571 | 0.678 |
| 15000 | 29.25K | −83.58 | 3271 | −29067 | 0.308 |
| 20000 | 22.08K | −83.69 | 2427 | −21946 | 0.175 |
| 30000 | 11.57K | −59.61 | 5853 | −9980 | 0.053 |
| 30400 | 15.57K | −44.95 | 11019 | −11000 | 0.058 |
| 32600 | 16.55K | −78.86 | 3198 | −16238 | 0.079 |
| 40000 | 12.8K | −84.94 | 1129 | −12750 | 0.051 |
| 50000 | 9.99K | −85.1 | 853 | −9953 | 0.032 |

As shown here, if the up-conversion process is applied at 40 kHz, the capacitive reactance is only about 13 k, where the inductance needed to cancel it is only about 50 mH (a practical value for this frequency) including parasitics. The resistive impedance left is only about 1 kΩ.

This means that much more low-frequency signal power can be obtained from the use of this internally-injected up-conversion type of sensor compared to sensors not having this modification. In particular embodiments, a 5 pT peak-to-peak signal may translate to about 85 nV or about 30 nV RMS. The available power from a 1 k impedance is about −151 dBm, and the amount of thermal noise in a 1 Hz bandwidth is about −174 dBm. At this frequency, a 1 dB noise figure is easily obtained. Therefore, with a bandwidth of 5 Hz, the SNR is about 15 dB with no event averaging, right out of the AFE. As a result, signal conditioning circuitry can be fabricated that does not substantially limit the ability to detect an excellent low frequency signal.

Note that the use of a sine wave-injected carrier is for illustration only. For example, in other embodiments, the sine current waveform can be replaced by a substantially or completely square waveform. With this type of waveform, the sensor 800 is either completely on or completely off for most of the time. Also, a square wave injection (as opposed to a sine wave injection) may increase the conversion gain and overall system sensitivity by 6 dB. Further, in some embodiments, biasing the sensor's net magnetic field off with the electromagnet may be better than biasing the sensor's net magnetic field on. This is because the electromagnet's current may have noise associated with it, which would be irrelevant as the sensor is inactive at that time. During the other half-cycles, the electromagnet's current and its noise are shut off, while the inherently quiet permanent magnet(s) 808*a*-808*b* is/are the sole supplier of bias to sensitize the sensor 800.

Figure 12:
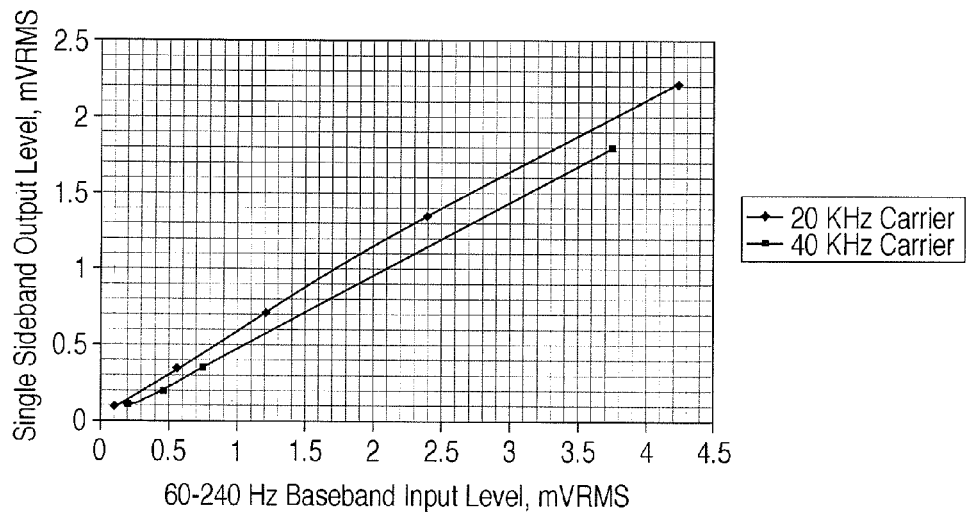

FIG. 12 illustrates heterodyning transfer characteristics of an example implementation of the sensor 800. This shows that the up-conversion process is substantially linear with respect to the output band versus the input band at both 20 kHz and 40 kHz. Single sideband loss could be about 6 dB, so double sideband loss would be about 0 dB. Note that it has been shown that this up-conversion process can be substantially linear both in amplitude and in phase (time delay constant with frequency).

In particular embodiments, the sensor 800 of FIG. 8 can operate at resonance. At a certain frequency, the propagation time across the dimension of the piezo-electric material equals 0.5 wavelength. At this frequency, a resonance effect causes the piezo-electric material to produce a significantly higher output voltage (such as at least 20 times more) per unit strain. Such large transducer gain can make front-end noise negligible, such as down to fields of 10 pT. The ability to shift (up-convert or down-convert) from any frequency to the resonance frequency permits one to take advantage of this resonance effect, regardless of the frequency of magnetic fields being measured. In particular embodiments of the sensor 800, the resonance frequency may be about 32 kHz, although the exact resonance frequency varies depending on the structure of the sensor.

Figure 13:
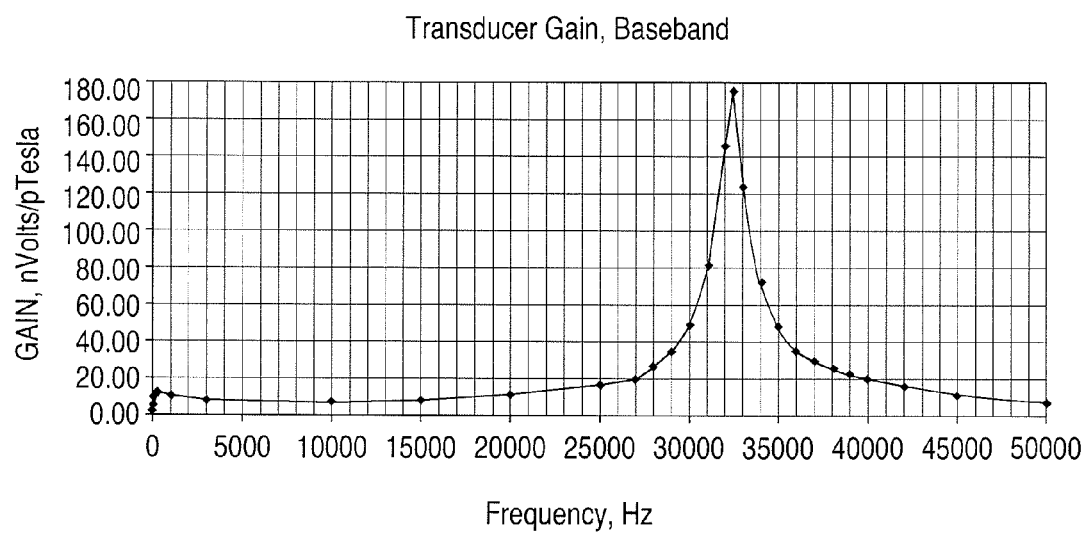

FIG. 13 illustrates transducer gain of an example sensor 800 as a function of frequency for a particular implementation of the sensor 800. As shown in FIG. 13, except for frequencies within influence of the resonance point, the transducer gain appears to be within the range from about 6 nV/pT to about 11 nV/pT. However, the gain at the resonance frequency, 32.4 kHz in this example, is significantly larger at close to 180 nV/pT. Other sensors (such as those having a larger number of piezo-electric and magneto-strictive layers and a plastic enclosure with plastic end caps and an aluminum foil lining) could have even higher transducer gain at resonance, such as close to 500 nV/pT.

Note that while up-conversion (including to the sensor's resonance frequency) is discussed above, down-conversion in general and down-conversion to the sensor's resonance frequency in particular can also be performed. For example, there may be some situations for which it is desired to measure the strength of a magnetic field whose frequency is above the sensor's resonance frequency. By down-converting to the sensor's resonance frequency, the SNR of the sensor could again be improved.

Figure 14:
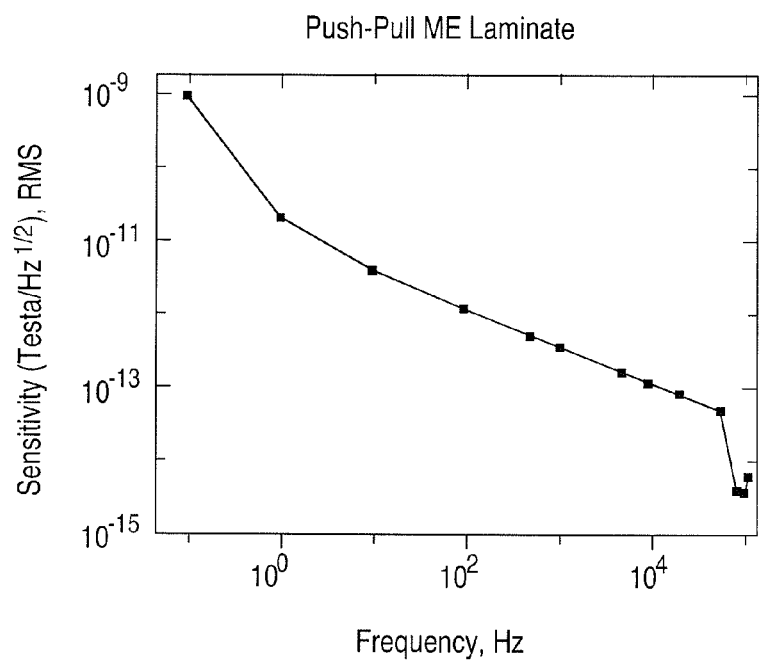

FIG. 14 illustrates the noise spectra reported for a conventional magneto-electric sensor (without injected up-conversion). The noise floor density versus frequency shown here may not be that of the sensor but that of signal conditioning electronics used with the sensor. Because of this, the use of injected up-conversion could permit the 3 Hz (low) frequency noise floor (which here is 10 pT/Hz$^{0.5}$) to equal that of the 40 kHz (high) frequency noise floor (which here is 100 fT/Hz$^{0.5}$).

It has been surmised that almost all or at least a significant portion of the noise in this sensor structure comes from the piezo-electric material, rather than from the magneto-strictive material. It has been shown that the sensor as a whole is much quieter at higher frequencies than at lower frequencies. Such knowledge forms part of the basis for expecting to achieve better sensitivity through the use of the frequency up-conversion or down-conversion process and is in addition to the impedance advantage discussed above. Inasmuch as a frequency up-conversion or down-conversion process occurs before a signal reaches the piezo-electric material, the signal can already be at a frequency where the piezo-electric material is quieter when it reaches this/these layer(s). It has been shown that the SNR at the sensor's resonance is approximately 10 dB higher than when the sensor is not in resonance. In addition to making the sensor more sensitive at resonance, this fact supports the supposition that most or all of the noise comes from the piezo-electric material.

The sensor 800 shown in FIG. 8 can be used in a wide variety of applications, including heart monitoring applications. However, the sensor 800 is not limited to use in just heart monitoring applications. For example, the sensor 800 could be used for sensing or measuring magnetic fields from other parts of the body or from very small currents in electronic circuits or in any other application requiring the detection or measurement of extremely weak magnetic fields or currents at a distance.

The sensor 800 has been described above as using one or more permanent magnets and one or more electromagnets to create a time-varying biasing magnetic field within the sensor 800. However, other techniques could be used to generate the time-varying biasing field. For example, one or more permanent magnets that move within or outside of the sensor 800 could be used to generate a time-varying magnetic field within the sensor 800, and the electromagnet could be omitted. As a particular example, one or more permanent magnets could be moved with back and forth translation so that the sensor would vary from strongly on to almost or completely off. As another particular example, one or more permanent magnets could be rotated to yield a balanced modulator type of response. As yet another particular example, one or more fixed permanent magnets could be used with one or more movable permanent magnets (such as rotatable magnets) to generate a total biasing field that has a raised cosine shape. Another way to generate a time-varying biasing magnetic field is to use one or more electromagnets that are controlled as described above (such as with a sine or square wave) without any permanent magnets. In each of these embodiments, as with the use of both permanent magnet(s) and electromagnet(s), the frequency up-conversion or down-conversion is occurring within the sensor itself.

In other embodiments, the frequency up-conversion or down-conversion could be achieved by chopping the surrounding magnetic field that is being measured by the sensor or otherwise performing the up- or down-conversion prior to the sensor. For example, the sensor could be moved (such as rotated or translated) relative to the magnetic field being measured. As another example, the sensor could be intermittently shielded from the surrounding magnetic field to be measured. This could be accomplished by using a shutter, such as a slotted disc, made from a magnetic shielding material like Mu metal. The slotted disc could spin in order to alternatively transmit and block the low-frequency magnetic field being measured. The sensor could also be encased in a magnetic shielding material so that the surrounding magnetic field only reaches the sensor through the slotted disc. In these embodiments, the sensor 800 may or may not include a time-varying biasing magnetic field, such as one produced using an electromagnet.

In still other embodiments, one or more electromagnets without permanent magnets could be used to repeatedly reverse the polarity of the sensor's output. The electromagnet's drive current in this case could have no DC component. This causes the sensor to act as a balanced modulator with a small output at the carrier frequency. For the embodiment of the sensor used with respect to FIG. 2 above, this could be achieved by applying to the solenoid 812 a sine or square wave symmetric around 0 A and having a peak-to-peak range of about 1.2 A.

In general, all of these embodiments are characterized by the fact that the up-conversion or down-conversion is performed before the surrounding magnetic field is converted into an electrical signal within the sensor. The up-conversion or down-conversion could involve the use of a time-varying biasing magnetic field, a time-invariant biasing magnetic field, a chopped magnetic field to be measured, or any suitable combination thereof. As long as the up-conversion or down-conversion is performed before the surrounding magnetic field is converted into an electrical signal, at least some of the benefits previously discussed remain, regardless of the mechanism by which the up-conversion or down-conversion is achieved.

Although FIGS. 7 and 8 illustrates examples of magneto-electric sensors, various changes may be made to FIGS. 7 and 8. For example, the sensors 700 and 800 could include any number of magneto-strictive and piezo-electric layers. The sensor 800 could also include any number of permanent magnets, electromagnets, and other components in any suitable configuration. As a particular example, the electromagnet's windings within the sensor could be arranged so that, with the correct drive current amplitude and/or phasing, the frequency conversion carrier signal seen at the sensor output along with the information-carrying sidebands could be reduced in level. The sensor 800 could further include any suitable electromagnet(s) for reducing or cancelling the biasing magnetic field from the permanent magnet(s). Although FIGS. 9 through 14 illustrate additional details of example embodiments of the sensor 800 or 700, these details are for illustration only. Embodiments of the sensor 800 or 700 could operate in ways other than as shown in FIGS. 9 through 14.

Figure 15:
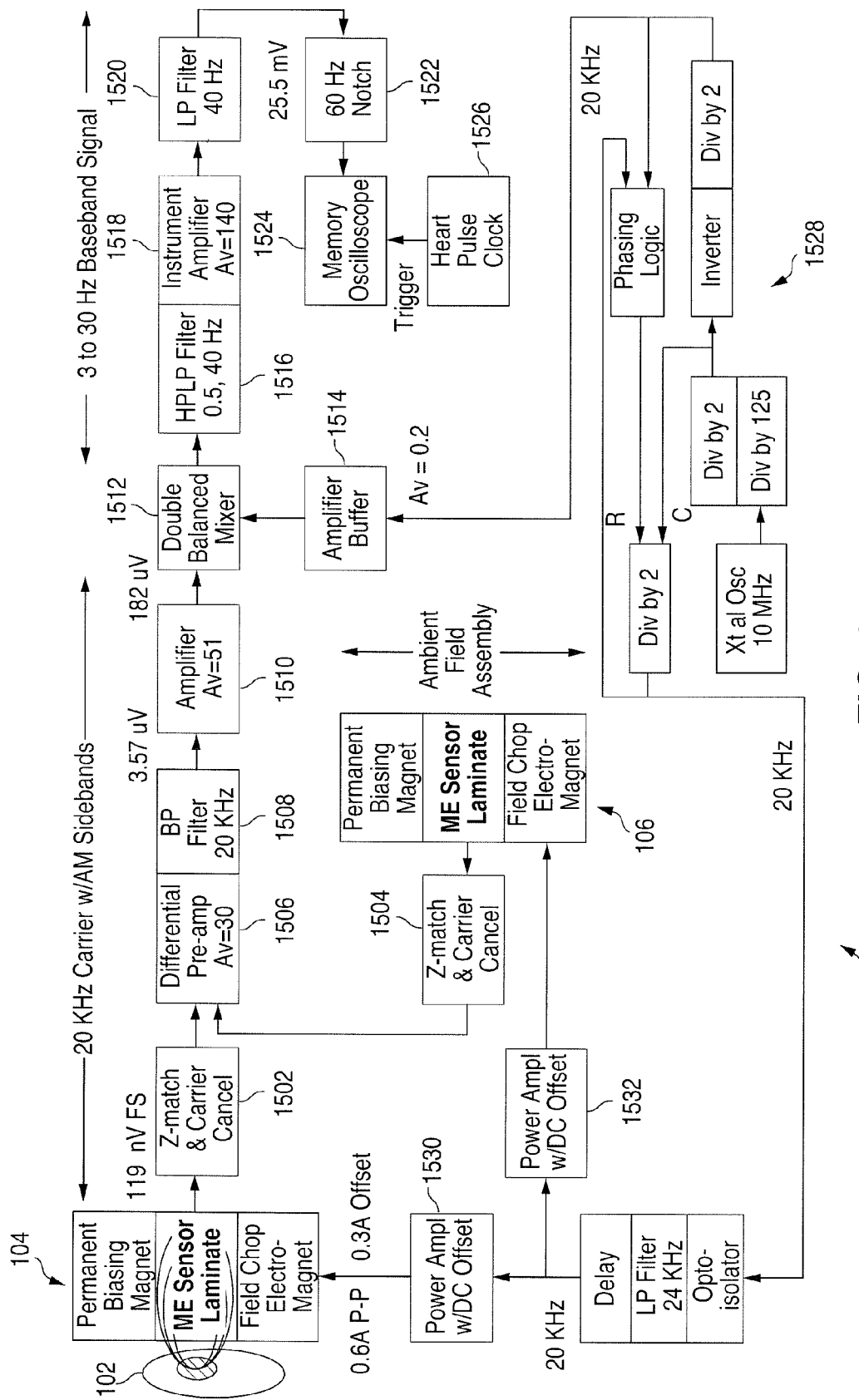
FIGS. 15 through 17 illustrate example systems for measuring magnetic fields using magneto-electric sensors with up-conversion or down-conversion according to this disclosure.
Figure 16:
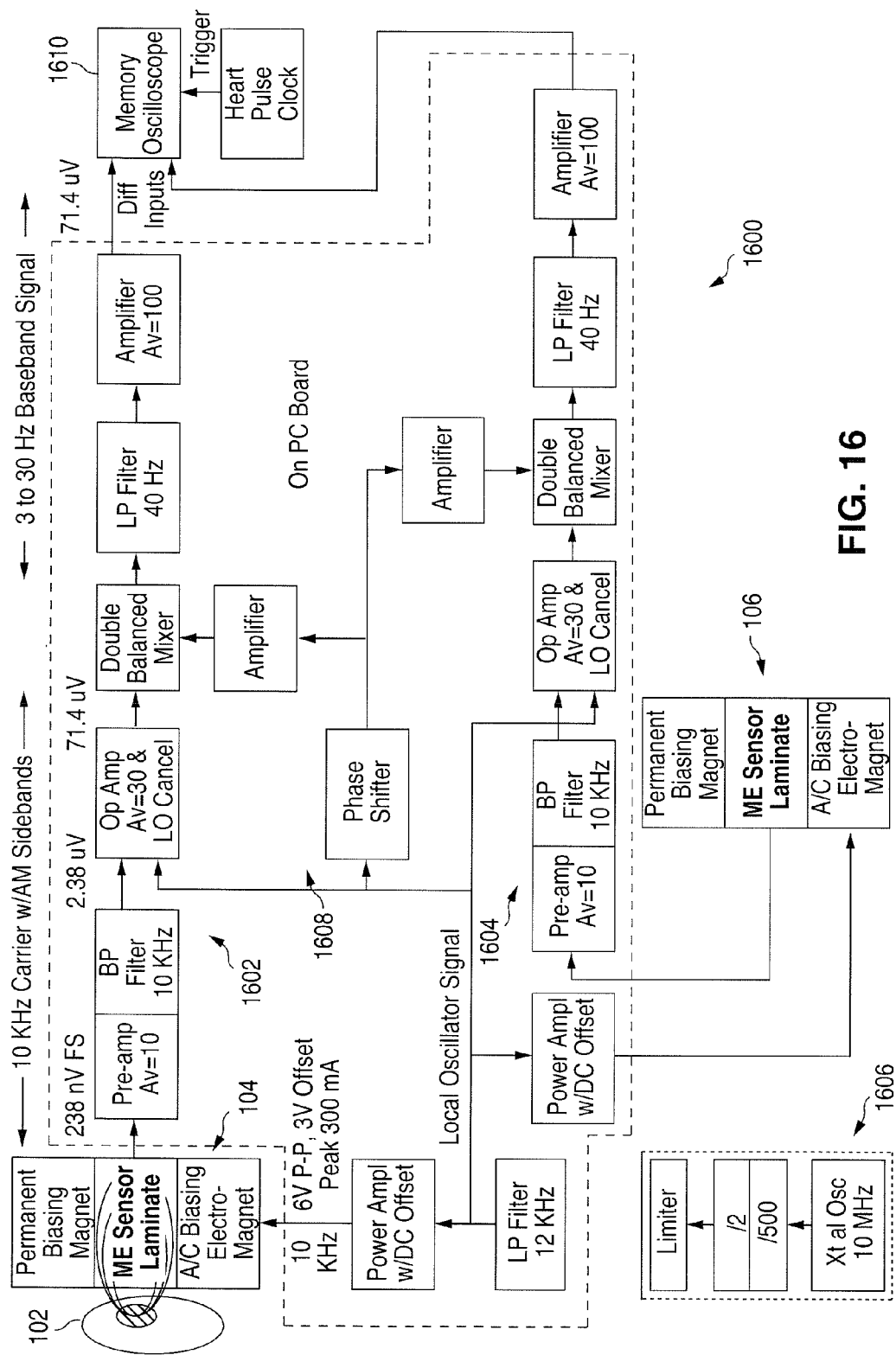
Figure 17:
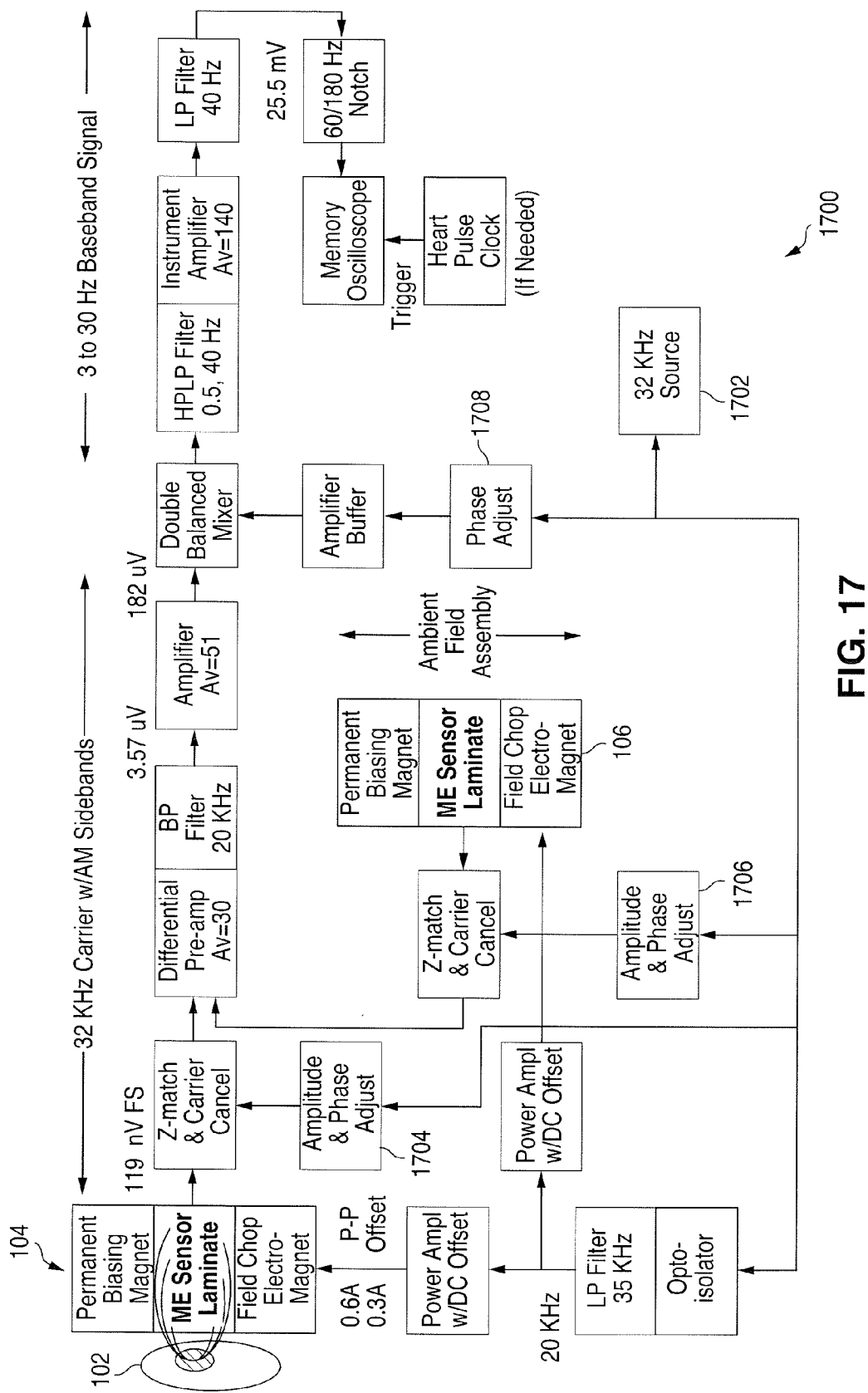

FIGS. 15 through 17 illustrate example systems for measuring magnetic fields using magneto-electric sensors with up-conversion or down-conversion according to this disclosure. As shown in FIG. 15, a system 1500 includes magnetic field sensors 104-106 that could represent multiple sensors 800 from FIG. 8. Each sensor 104-106 has a permanent biasing magnet and a "field chopping" electromagnet. As before, the sensor 104 senses the very weak low frequency varying myocardial magnetic field (or from any other application of this sensor), and both sensors 104-106 sense ambient magnetic fields.

One or more matching networks 1502-1504 are coupled between the sensors 104-106 and a front-end differential pre-amplifier 1506. The pre-amplifier 1506 cancels signals from the ambient magnetic field having in-band frequency components that cannot be filtered out. The pre-amplifier 1506 can also cancel microphonics (ambient vibrations detected by piezo-crystal elements). An output of the pre-amplifier 1506 is processed by a bandpass filter 1508 and an amplifier 1510. The pre-amplifier 1506 could have a gain of 30, the bandpass filter 1508 could be centered at 20 kHz (the same as the carrier frequency used by the sensors 104-106), and the amplifier 1510 could have a gain of 51.

An output of the amplifier 1510 is provided to a down-converting double balanced mixer 1512, which mixes the output of the amplifier 1510 with a normal or inverted version of the carrier signal provided by a buffer 1514. A high-pass, low-pass (HPLP) filter 1516 filters a mixed output of the mixer 1512, such as above 0.5 Hz and below 40 kHz. An output of the filter 1516 is processed by an instrumentation amplifier 1518, a low-pass filter 1520, and a set of one or more notch filters 1522 before being presented on a memory oscilloscope 1524. The amplifier 1518 could have a gain of 140, the low-pass filter 1520 could pass signals below 40 kHz, and the filter 1522 could represent a 60 Hz notch filter and/or notch filtering of 60 Hz harmonics. The memory oscilloscope 1524 is triggered by a heart pulse clock 1526, such as a pulsimeter or 3-lead ECG.

In this example, circuitry 1528 is used to generate the 20 kHz carrier signal used by the up-converting sensors 104-106. The circuitry 1528 includes frequency dividers, an inverter, and phasing logic for converting a 10 MHz clock signal from a crystal oscillator into two 20 kHz signals. One 20 kHz signal is provided to the sensors 104-106, and the other 20 kHz signal (possibly inverted) is provided to the buffer 1514.

Power amplifiers with DC offset 1530-1532 help to ensure that there is a proper phase relationship between the carrier input to the mixer 1512 and the carrier signal entering the sensors' electromagnets. The phase relationship between the carrier signal entering the sensors' electromagnets and the carrier input to the mixer 1512 depends upon whether amplitude or phase/frequency information is desired and stray phase shifts within the circuitry between these two blocks. The amplifiers 1530-1532 could be implemented using drive transistors.

In the embodiments of the various systems described prior to FIG. 15, only the low frequency baseband signal is present at the sensor outputs, and pre-amplifiers preceded a difference amplifier in order to have the lowest possible noise figure. For the embodiment shown in FIG. 15, the difference amplifier (here a pre-amplifier 1506) can immediately follow the sensors 104-106, thus eliminating any other duplication of signal chain circuitry.

Inasmuch as the mixing action of the chopped sensor biasing is not balanced, a large carrier signal (20 kHz in this example) comes from each sensor output along with the coherent upper and lower sidebands. These sidebands represent the desired low frequency AC magnetic field in the "heart" sensor 104 and the vibration pickup and ambient low frequency AC magnetic fields in both sensors 104-106. Substantially all of the above signals (except for the heart signal) are cancelled in the differential pre-amplifier 1506. As noted above, the pre-amplifier 1506 does not require extremely high input impedance since the sensors' reactance could be only about 25 kΩ at 20 kHz. Also, at that frequency, 1/f noise is not a significant issue.

Following adequate signal amplification (such as to ensure the lowest possible system noise figure but small enough to prevent overload of the mixer 1512 by remnants of the carrier frequency coming from the sensors 104-106 and remnants of power at 20 kHz±60 Hz), the combined signal is fed to the double balanced mixer 1512. In order for the mixer 1512 to function as a synchronous detector of the low frequency baseband signal, it can receive a 20 kHz carrier signal into its Local Oscillator (LO) input of equal or opposite phase as that of the signal input. In this design, the mixer signal input phase is equal or opposite to the phase of the current entering the sensor electromagnets. This current could lag the voltage feeding the drive transistors by 90°, so the mixer LO signal can also lag by 90° to compensate. If the total phase shift is equal or opposite, the amplitude of the desired signal is captured. If the total phase shift is plus or minus 90°, the phase/frequency is captured.

Since the up-conversion and down-conversion LO sources are co-located and co-sourced, no phase-locked loops (PLLs) are needed to provide coherence. Moreover, both phase and amplitude carrier noise can be cancelled out if necessary. Further, since only amplitude may be detected (assuming the correct phase relationships as stated above) in the synchronous detector, phase noise on the 20 kHz carrier is of no consequence. Nevertheless, a high-quality crystal oscillator can be employed as the source, and its phase noise can be divided down by various frequency dividers. Amplitude noise on the carrier, especially so close to the carrier (±3 Hz), can be controlled if not cancelled out, but this can be accomplished by the limiting action of the frequency dividers.

Following the down-converting double balanced mixer 1512, the low frequency baseband signal is high-pass and low-pass filtered and further amplified to be of high enough level for the memory oscilloscope 1524. The 60 Hz remnant may still be stronger than the myocardial magnetic signal, so the signal can be fed through the set of notch filters 1522 (such as 60 Hz and harmonics filters) prior to the oscilloscope. In addition to signal cancellation of ambient fields, various magnetic shielding techniques can also be employed.

Lacking further analog or digital signal processing, if the myocardial MCG signal is too noisy to be suitable, multiple event averaging can be available by triggering the memory oscilloscope 1524 with the heart pulse clock 1526 that locates the same feature of the heart wave with each beat. Thus, the heart signal can retrace the same spot on a screen with each beat, whereas the noise can be scattered more uniformly around the screen.

As shown in FIG. 16, a system 1600 omits a differential amplifier/pre-amplifier, and the system 1600 includes dual circuit paths 1602-1604 for processing the sensor readings from the sensors 104-106. Each circuit path 1602-1604 here includes a pre-amplifier, a bandpass filter, an operational amplifier with local oscillator cancelation, a double balanced mixer, a low-pass filter, and an amplifier. Also, a 10 kHz carrier signal is generated using circuitry 1606 that includes frequency dividers, a limiter, and a low-pass filter. The carrier signal is provided to the dual circuit path 1602-1604 via circuitry 1608 that includes a phase shifter and two amplifiers. In this example, a memory oscilloscope 1610 receives and processes differential input signals from the dual circuit path 1602-1604. In this example, the dual circuit paths 1602-1604, the circuitry 1608, and various other components can reside on a single printed circuit board (PCB).

As shown in FIG. 17, a system 1700 is similar in structure to the system 1500 shown in FIG. 15. One minor difference between the two systems is that the system 1700 uses a clock source 1702, which provides a 32 kHz carrier signal. The carrier signal is provided to two amplitude and phase adjust units 1704-1706, which can adjust the amplitude and phase of the carrier signal. The adjusted carrier signals can be used for impedance matching and carrier cancellation. The carrier signal is also provided to a phase adjust unit 1708, which can adjust the phase of the carrier signal prior to down-conversion mixing. The adjust units 1704-1708 can be used to help ensure proper operation of the circuitry in FIG. 17.

One advantage of the architecture in FIG. 17 over the previous two architectures is that cancellation of the carrier signal from each separate sensor can be effected separately from the cancellation of in-band interfering magnetic fields that exhibit the same flux density at each sensor. This independence can be useful as the carrier cancelling signals may need to have different levels and/or phases, and the transducer gains of the sensors may differ.

In particular embodiments, the system 1700 can be implemented using three integrated circuit (IC) chips. One IC chip can include the clock source. Another IC chip can include the power amplifiers with DC offset. A third IC chip can include the remaining components in FIG. 17, except for the sensors 104-106, an opto-isolator, a 20 kHz bandpass filter, a memory oscilloscope, and a heart pulse clock.

Regarding down-conversion (such as in the mixers of FIGS. 15-17), transducer gain can fall off above a certain frequency, such as about 50 kHz. While at these high frequencies, the low reactance of each magneto-electric sensor's equivalent output capacitance presents no problem with coupling energy to a connector, and the source of this transducer gain fall-off may be within the piezo-electric region. If so, down-conversion to a lower frequency, especially the resonance frequency, can result in a large increase of overall gain and sensitivity. For instance, if magnetic field studies at 150 kHz are undertaken, the injection frequency 118 kHz could produce energy at a 32 kHz resonance frequency.

Although FIGS. 15 through 17 illustrate example systems for measuring magnetic fields using magneto-electric sensors with up-conversion or down-conversion, various changes may be made to FIGS. 15 through 17. For example, multiple channels can be used in each system. Also, the functional divisions shown in FIGS. 15 through 17 are for illustration only. Various components in each figure could be combined, omitted, or further subdivided and additional components could be added according to particular needs.

Further, various systems described above have shown the use of specific values (such as capacitances, resistances, inductances, reactances, frequencies, and noise levels). However, these specific values are for illustration only. Each of these values is approximate, and all of these values are based on specific implementations of particular circuits or systems. Other circuits or systems that have different component values or other values can be used without departing from the scope of this disclosure. In addition, features shown in one or more systems described above could be used in other systems described above.

Depending on the implementation, these types of systems could have the following benefits or advantages. The systems can be portable, non-invasive, and easy and quick to set up. They can store a large amount of data (in an internal or external memory or other storage device) and be relatively lower in cost. The systems can be contact-free, meaning no leads need to be attached to a patient. No radiation is needed and no side effects may exist to the contactless measurement of magnetic fields from the patient's heart. Minimal approval may be required from regulatory agencies such as the U.S. F.D.A., no cryogenic cooling is required, and more information (such as measurements of vortex magnetic currents) can be obtained compared to conventional ECGs. The measurements from the systems can be easily repeated, and the data can be highly reliable (assuming the patient complies with instructions such as to remain still for 10-15 seconds). The systems can capture large amounts of data and provide real-time measurements. In addition, this allows earlier detection of dangerous heart conditions.

These types of systems have a wide variety of uses and are not limited to heart analysis applications or even to medical applications. Similar types of systems could be used in a wide variety of applications, such as medical imaging, non-invasive medical sensing, precision navigation, mineral prospecting, and detection of pathogens (to name a few). Example medical imaging applications include medical imaging, such as brain function mapping, blood flow CCD imaging, and neural mapping. Some examples of non-invasive biomagnetic medical applications include magneto-cardiogram, magneto-encephalogram, magneto-myogram, and magneto-oculogram sensing. An MCG could be used to replace an ECG. A magneto-encephalogram can allow the measurement of brain activity without the need for probes connected to the patient's head. A magneto-myogram may eliminate the need for using painful needles to measure muscular activity. A magneto-oculogram may allow contactless measurements of electrical signals originating from the eyes. Brain function mapping may allow for contactless 2D and 3D mapping of the brain for sleep disorders, detecting brain tumors, identifying locations of epileptic seizures, and detecting strokes (to name a few uses). The 2D and 3D mapping may provide valuable clues to doctors in assisting patients with spinal injuries, muscular dystrophy, and other neural and neuromuscular injuries or diseases. A blood flow CCD imager may allow for sensing blood flows in hard-to-scan organs (such as the liver, pancreas, or intestines) to perform early detection of blood clots in arteries. Also, cancerous cells in these organs often have increased blood flow capillaries towards hard-to-detect tumorous areas. Other medical sensing applications can include iron concentration or iron deficiency sensing for blood samples and pathogen detection (such as bacterial detection) for blood or other fluids, liquids, and food. Example mineral prospecting applications could include detecting specific geological locations for "precision" oil drilling.

Note that these types of systems can perform a wide variety of computations or signal processing functions and are not limited to just calculating the positive and negative peak amplitudes of T-waves. For example, systems could examine locations of the spectrum where a T-wave and its derivative appear as "harmonics" related to width. These spectral components are higher in frequency and away from the noise, but are also generally weak. These components could be analyzed to determine one or more conditions or perform other functions. As another example, the QRS complex precedes the T-wave, and the QRS complex has a very high dv/dt and can be used as an internal standard separately for each heartbeat, for both timing and amplitude purposes. As a third example, when the T-wave is relatively intact riding on the slowly-varying noise floor, the absolute levels of the T-waves could be disregarded, and the difference between the T-wave peak and the heart waveform's "baseline" value could be used during analysis. For instance, the field instrument could sample the waveform value just after the S wave and use it as the baseline value to process the following T-wave.

Figure 18:
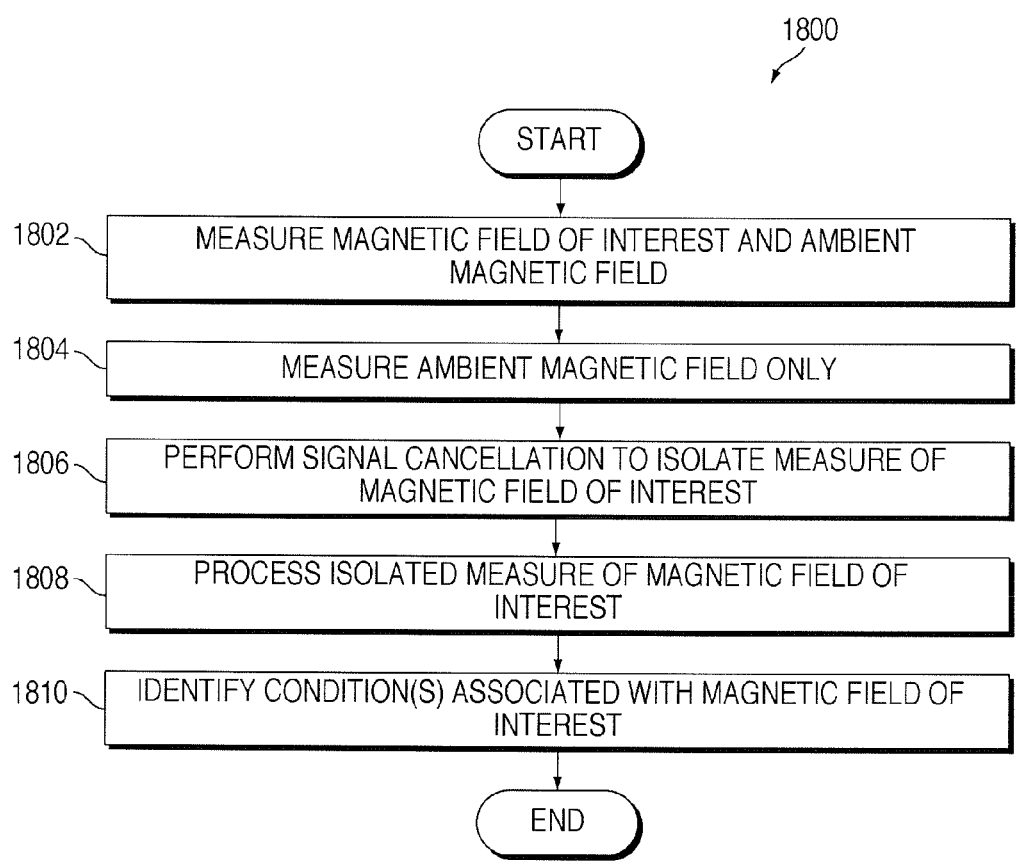
FIG. 18 illustrates an example method for measuring magnetic fields according to this disclosure.

FIG. 18 illustrates an example method 1800 for measuring magnetic fields according to this disclosure. As shown in FIG. 18, a magnetic field of interest and an ambient magnetic field are measured at step 1802, and the ambient magnetic field only is measured at step 1804. These steps could involve the use of magneto-electric sensors, magneto-electric sensors with up-conversion, or any other suitable sensors.

Signal cancellation is performed to isolate the measure of the magnetic field of interest at step 1806. This could include, for example, providing the signals from the sensors to a difference amplifier. The signals may or may not be amplified, such as by using pre-amplifiers.

The isolated measure of the magnetic field of interest is processed at step 1808, and one or more conditions associated with the magnetic field of interest are identified at step 1810. This could include, for example, performing any necessary filtering, amplification, mixing, and other signal processing operations. This could also include, for a heart monitoring application, isolating T-waves or other features of a patient's heart waveform and obtaining information about the identified T-waves. As a particular example, this could include identifying the amplitudes of alternate beat T-waves and determining whether the amplitudes differ by a specified amount. Note, however, that any other suitable processing could occur, such as processing to identify other features of a patient's heart waveform or other features of some other signal.

Although FIG. 18 illustrates an example method 1800 for measuring magnetic fields, various changes may be made to FIG. 18. For example, various steps in FIG. 18 could overlap, occur in parallel, occur in a different order, or occur multiple times.

It may be advantageous to set forth definitions of certain words and phrases that have been used within this patent document. The term "couple" and its derivatives refer to any direct or indirect communication between two or more components, whether or not those components are in physical contact with one another. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "controller" means any device, system, or part thereof that controls at least one operation. A controller may be implemented in hardware, firmware, software, or some combination of at least two of the same. The functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A system comprising:
at least one first magnetic field sensor configured to measure first and second magnetic fields;
at least one second magnetic field sensor configured to measure the second magnetic field substantially without measuring the first magnetic field;
wherein the first and second magnetic field sensors comprise magneto-electric sensors, each magneto-electric sensor comprising alternating layers of magnetostrictive material and piezo-electric material;
wherein each magneto-electric sensor further comprises:
a magnet configured to sensitize the sensor;
an electromagnet configured to at least partially desensitize the sensor;
wherein the electromagnet in each magneto-electric configured sensor is configured to receive a carrier signal;
the at least one first magnetic field sensor is configured such that the carrier signal modulates the biasing magnetic field thereby emulating an up-converting heterodyne mixer, wherein the low frequency magnetic field signal is outputted from the sensor as coherent sidebands near the carrier frequency;
the at least one second magnetic field sensor is configured such that the carrier signal modulates the biasing magnetic field thereby emulating an up-converting heterodyne mixer, wherein the low frequency magnetic field signal is outputted from the sensor as coherent sidebands near the carrier frequency;
thereby repeatedly sensitizing and at least substantially desensitizing the at least one first and second magnetic field sensors; and
processing circuitry configured to perform signal cancellation to generate measurements of the first magnetic field and to generate an output based on the measurements of the first magnetic field.

2. The system of claim 1, wherein the first and second magnetic field sensors comprise one of: magneto-resistive sensors, magneto-electric sensors, giant magnetic tunneling junctions, spin-valve sensors, cesium vapor sensors, flux gate sensors, optically-pumped sensors, and micro-electro-mechanical system (MEMS) sensors.

3. The system of claim 1, wherein:
the system comprises multiple channels, each channel comprising one or more first magnetic field sensors; and
the system comprises a single second magnetic field sensor.

4. The system of claim 1, wherein the processing circuitry is configured to:
generate a waveform associated with a patient's heart;
identify T-waves in the waveform; and
determine whether a difference between average amplitudes of alternating beat T-waves exceeds a threshold.

5. The system of claim 1, wherein:
the processing circuitry is configured to generate and process a waveform associated with a patient's heart; and
the system further comprises a triggering unit configured to synchronize at least one of the processing circuitry and a display device with heartbeats of the patient.

6. An apparatus comprising:
a signal cancellation unit configured to:
receive signals from at least one first magnetic field sensor configured to measure first and second magnetic fields;
receive signals from at least one second magnetic field sensor configured to measure the second magnetic field substantially without measuring the first magnetic field; and
wherein the first and second magnetic field sensors comprise magneto-electric sensors, each magneto-electric sensor comprising alternating layers of magnetostrictive material and piezo-electric material;
wherein each magneto-electric sensor further comprises:
a magnet configured to sensitize the sensor;
an electromagnet configured to at least partially desensitize the sensor;
wherein the electromagnet in each magneto-electric configured sensor is configured to receive a carrier signal;
the at least one first magnetic field sensor is configured such that the carrier signal modulates the biasing magnetic field thereby emulating an up-converting heterodyne mixer, wherein the low frequency magnetic field signal is outputted from the sensor as coherent sidebands near the carrier frequency;
the at least one second magnetic field sensor is configured such that the carrier signal modulates the biasing magnetic field thereby emulating an up-converting heterodyne mixer, wherein the low frequency magnetic field signal is outputted from the sensor as coherent sidebands near the carrier frequency;
thereby repeatedly sensitizing and at least substantially desensitizing the at least one first and second magnetic field sensors;
the at least one first and second magnetic field sensors configured to perform signal cancellation to generate measurements of the first magnetic field; and
processing circuitry configured to generate an output based on the measurements of the first magnetic field.

7. The apparatus of claim 6, wherein the signal cancellation unit comprises a difference amplifier or a difference preamplifier.

8. The apparatus of claim 6, wherein:
the apparatus comprises multiple channels, each channel configured to receive signals from one or more first magnetic field sensors; and
the apparatus is configured to receive signals from a single second magnetic field sensor.

9. The apparatus of claim 6, wherein the processing circuitry is configured to:
generate a waveform associated with a patient's heart;
identify T-waves in the waveform; and
determine whether a difference between average amplitudes of alternating beat T-waves exceeds a threshold.

10. The apparatus of claim 6, wherein:
the processing circuitry is configured to generate and process a waveform associated with a patient's heart; and
the apparatus is further comprises to receive a trigger signal and synchronize with heartbeats of the patient.

11. The apparatus of claim 6, further comprising:
a carrier signal source configured to generate a carrier signal for electromagnets in the magnetic field sensors that operate to up-convert signals of interest in outputs of the magnetic field sensors.

12. The apparatus of claim 11, wherein the carrier signal source is configured to generate the carrier signal at a resonance frequency of the magnetic field sensors.

13. A method comprising:
receiving signals identifying first and second magnetic fields from at least one first magnetic field sensor;
receiving signals identifying the second magnetic field but substantially not the first magnetic field from at least one second magnetic field sensor;
performing signal cancellation to generate measurements of the first magnetic field; and
generating an output based on the measurements of the first magnetic field.

14. The method of claim 13, wherein generating the output comprises:
generating a waveform associated with a patient's heart;
identifying T-waves in the waveform; and
determining whether a difference between average amplitudes of alternating beat T-waves exceeds a threshold.

15. The method of claim 13, wherein:
the output comprises coherent sidebands associated with the first magnetic field around a frequency of the drive signal; and
the method further comprises performing down-conversion using the drive signal or an inverted version of the drive signal.

16. The method of claim 13, further comprising:
operating each of the first and second magnetic field sensors at its resonance frequency.

\* \* \* \* \*